US006303297B1

(12) United States Patent
Lincoln et al.

(10) Patent No.: US 6,303,297 B1
(45) Date of Patent: Oct. 16, 2001

(54) DATABASE FOR STORAGE AND ANALYSIS OF FULL-LENGTH SEQUENCES

(75) Inventors: Steve E. Lincoln, Redwood City; Tod M. Klingler, San Carlos; Janice Au-Young, Berkeley; Y. Tom Tang, San Jose; Richard D. Goold, San Francisco; Ingrid E. Akerblom, Redwood City; Jeffrey J. Seilhamer, Los Altos Hills; Phillip R. Hawkins, Mountain View; Lynn E. Murry, Portola Valley; Angelo M. Delegeane, Milpitas; Wendy B. Levine; Jennifer L. Hillman, both of Mountain View; Surya K. Goli, San Jose; Christina M. Altus, Palo Alto; Olga Bandman, Mountain View, all of CA (US); Samuel T. LaBrie, O'Fallon, MO (US); Purvi Shah, Sunnyvale, CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 08/969,987

(22) Filed: Nov. 13, 1997

Related U.S. Application Data

(63) Continuation-in-part of application No. 08/289,822, filed on Aug. 12, 1994, now abandoned, and a continuation-in-part of application No. 08/581,240, filed on Dec. 29, 1995, now Pat. No. 5,840,870, and a continuation-in-part of application No. 08/744,026, filed on Nov. 5, 1996, now Pat. No. 5,786,148, and a continuation-in-part of application No. 08/786,999, filed on Jan. 23, 1997, now Pat. No. 5,892,016, and a continuation-in-part of application No. 08/822,262, filed on Mar. 20, 1997, now Pat. No. 5,849,899, and a continuation-in-part of application No. 08/951,750, filed on Oct. 16, 1997, and a continuation-in-part of application No. 08/282,955, filed on Jul. 29, 1994, now Pat. No. 6,114,114, which is a continuation-in-part of application No. 08/187,530, filed on Jan. 27, 1994, now Pat. No. 5,840,484, which is a continuation-in-part of application No. 08/137,951, filed on Oct. 14, 1993, now abandoned, which is a continuation-in-part of application No. 08/179,873, filed on Jan. 11, 1994, now abandoned, which is a continuation-in-part of application No. 08/100,523, filed on Aug. 3, 1993, now abandoned, which is a continuation-in-part of application No. 07/977,780, filed on Nov. 19, 1992, now abandoned, which is a continuation-in-part of application No. 07/916,491, filed on Jul. 17, 1992, now abandoned.

(51) Int. Cl.$^7$ .................................................. C12Q 1/68
(52) U.S. Cl. .......................................... 435/6; 364/413.02
(58) Field of Search ...................... 435/6; 364/413.02; 702/19, 20

(56) References Cited

U.S. PATENT DOCUMENTS

| | | | |
|---|---|---|---|
| 4,882,268 | 11/1989 | Penman et al. ........................ | 435/5 |
| 5,081,584 | 1/1992 | Omichinski et al. .................... | 703/6 |
| 5,270,170 | 12/1993 | Schatz et al. ....................... | 435/7.37 |
| 5,364,759 | 11/1994 | Caskey et al. ......................... | 435/6 |
| 5,371,671 | 12/1994 | Andersen et al. ................... | 382/182 |
| 5,840,484 | * 11/1998 | Seilhamer et al. ....................... | 435/6 |

FOREIGN PATENT DOCUMENTS

91/19818    12/1991   (WO).

OTHER PUBLICATIONS

IntelliGenetics Suite, Release 5.4, Advanced Training Manual, 1993, IntelliGenetics, Inc., Mountain View, CA, pp. 1–1 through 1–16.*

Adams, Mark D., et al., "Complementary DNA Sequencing: Expressed Sequence Tags and Human Genome Project", *Science* (1991) vol. 252, pp. 1651–1656.

Date, C.J., *An Introduction to Database Systems,* vol. 1, 5th Edition, Addison–Wesley Publishing Company (1990), pp. 22–25, 42–45, 111–117, 144–153, and 249–273.

Davison, "Introduction to Molecular Biology Information Servers" *Sigbio Newsletter* (1991) vol. 11, pp. 1–6.

Fickett, James W., et al., "Development of a Database for Nucleotide Sequences", *Mathematical Methods for DNA Sequences,* CRC Press, Inc. (1989), pp. 1–34.

Frenkel, Karen A., "The Human Genome Project and Informatics", *Communications of the ACM* (1991) vol. 34, No. 11, pp. 41–51.

Ghossein, Ronald A., et al., "Prognostic Significance of Detection of Prostate–Specific Antigen Transcripts in the Peripheral Blood of Patients with Metastatic Androgen–Independent Prostatic Carcinoma" *Urology* (1997) vol. 50, No. 1, pp. 100–105.

Hara, Eiji, et al., "Subtractive cDNA Cloning Using Oligo(dT)$_{30}$–latex and PCR:Isolation of cDNA Clones Specific to Undifferentiated Human Embryonal Carcinoma Cells", *Nucleic Acids Research* (1991) vol. 19, No. 25, pp. 7097–7104.

(List continued on next page.)

*Primary Examiner*—James Martinell
(74) *Attorney, Agent, or Firm*—Bozicevic, Field & Francis LLP; Carol L. Francis

(57) ABSTRACT

The present invention is a computerized storage and retrieval system for genetic information and related annotated information. The data of the system is stored in a relational database which interfaces with public databases to allow analysis both within the database of the invention and between information within that database and external public databases. The sequence data is edited before entry into the system, and is stored in a curated, functional clustering organization. The information associated with the data is stored in an expression database that is linked to the storage of the sequence data.

27 Claims, 18 Drawing Sheets

OTHER PUBLICATIONS

Hoog, Christer, "Isolation of a Large Number of Novel Mammalian Genes by a Differential cDNA Library Screening Strategy", *Nucleic Acids Research* (1991) vol. 19, No. 22, pp. 6123–6127.

Katso, Roy M.T., et al., "Molecular Approaches to Diagnosis and Management of Ovarian Cancer" *Cancer Metastasis Reviews* (1997) vol. 16, pp. 81–107.

Khan, Akbar S., et al., "Single Pass Sequencing and Physical and Genetic Mapping of Human Brian cDNAs", *Nature Genetics* (1992) vol. 2, pp. 180–185.

Matsubara, K., et al., "Identification of New Genes by Systematic Analysis of cDNAs and Database Construction", *Current Opin. Biotech.* (1993) vol. 4, pp. 672–677.

McCabe, et al., "Amplification of Bacterial DNA Using Highly Conserved Sequences: Automated Analysis and Potential for Molecular Triage of Sepsis", *Pediatrics* (1995) vol. 95, No. 2, pp. 165–169.

Okubo, et al., "Large Scale cDNA Sequencing for Analysis of Quantitative and Qualitative Aspects of Gene Expression", *Nature Genetics* (1992) vol. 2, pp. 173–179.

Pantanjali, Sankhavaram R., et al., "Construction of a Uniform–Abundance (Normalized) cDNA Library", *Proc. Natl. Acad. Sci. USA* (1991) vol. 88, pp. 1943–1947.

Porter–Jordan, Kathleen, et al., "Overview of the Biologic Markers of Breast Cancer" *Hematology/Oncology Clinics of North America* (1994) vol. 8, No. 1, pp. 73–100.

Rubenstein, John L.R., et al., "Subtractive Hybridization System Using Single–Stranded Phagemids with Directional Inserts", *Nucleic Acids Research* (1990) vol. 18, No. 16, pp. 4833–4842.

* cited by examiner

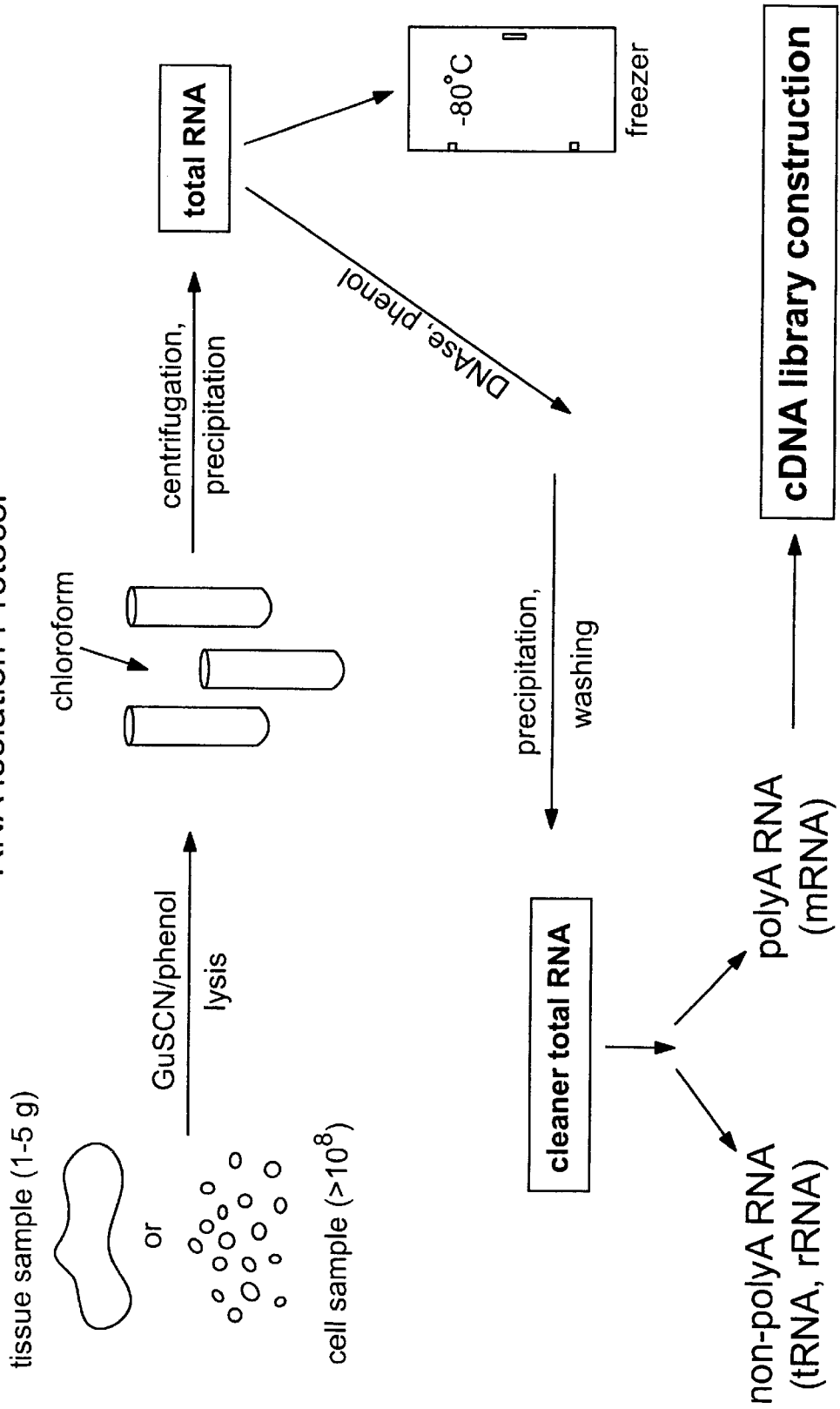

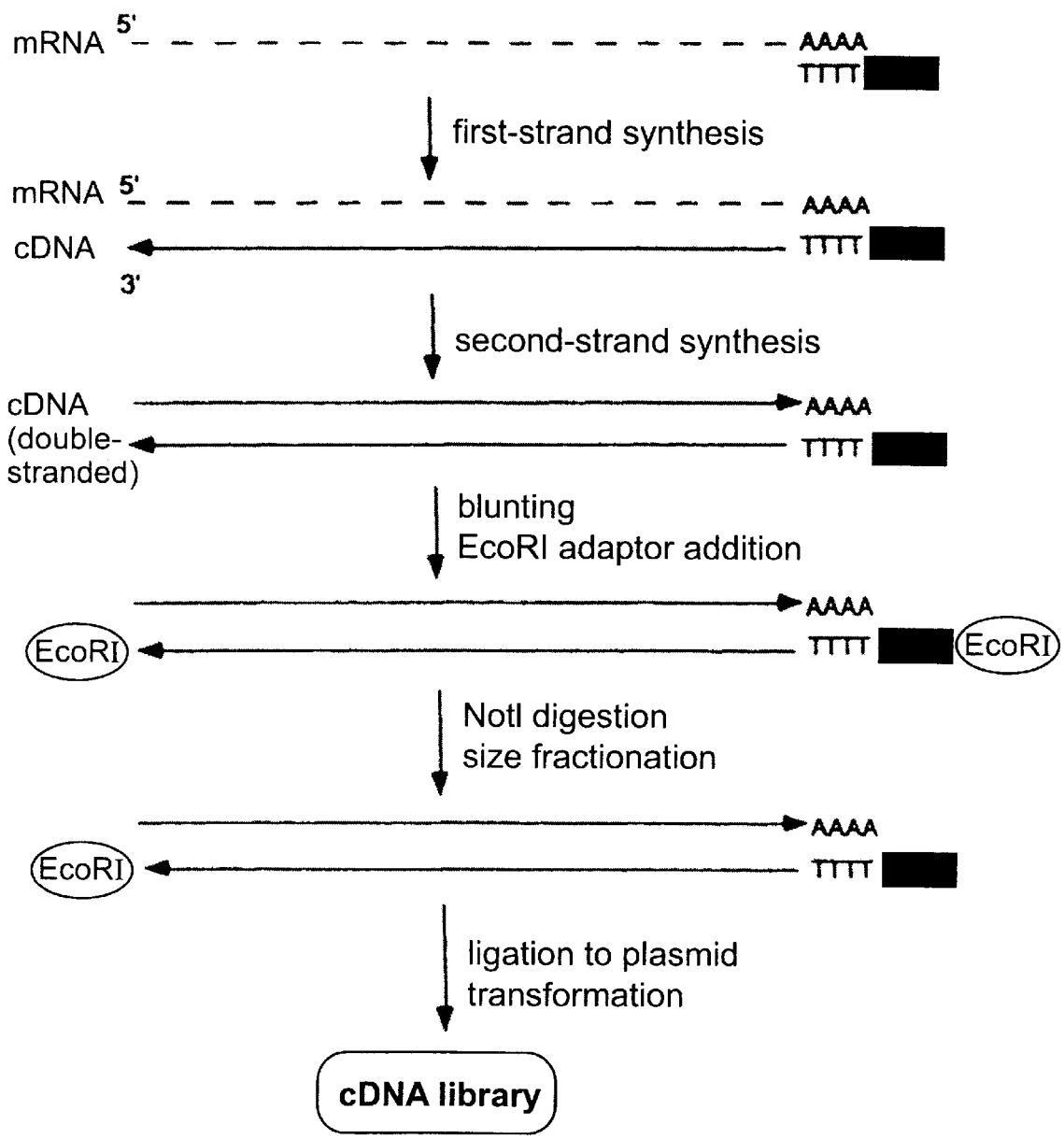

Block 1 Sequence Editing Screens

| Target Sequence Feature | Editing Method | Result |
|---|---|---|
| 5' and 3' Vector | Dynamic Programming | Clip |
| PolyA Tail | Regular Expression | Clip |
| Sequencing Artifacts | Nearest Neighbor | Remove |
| Low Information | BLAST (S ≥ 90) | Mask |
| Contamination | BLAST (S ≥ 90) | Remove |
| Repetitive Elements | BLAST (S ≥ 90) | Mask |
| Mitochondrial | BLAST (S ≥ 90) | Remove |
| Ribosomal RNA | BLAST (S ≥ 90) | Remove |

Aberrant

|   | A | C | G | T |    |
|---|---|---|---|---|----|
| A | 32 | 8 | 8 | 8 | 56 |
| C | 8 | 32 | 8 | 8 | 56 |
| G | 8 | 8 | 32 | 8 | 56 |
| T | 8 | 8 | 8 | 32 | 56 |
|   | 56 | 56 | 56 | 56 | 224 |

Expected

|   | A | C | G | T |    |
|---|---|---|---|---|----|
| A | 14 | 14 | 14 | 14 | 56 |
| C | 14 | 14 | 14 | 14 | 56 |
| G | 14 | 14 | 14 | 14 | 56 |
| T | 14 | 14 | 14 | 14 | 56 |
|   | 56 | 56 | 56 | 56 | 224 | e.g. CCCCGGGGTTTTCCCCAAAAGGGG...

FIG. 5

Rigorous Statistics:

$$E = KNe^{-\lambda S} \text{ where } S = \sum_{HSP} s(a_i, b_j)$$

$s(a,a) = 5$ and $s(a,b) = -4$ for $a \neq b$

FIG. 6

| Query | Match | BLAST Score | % ID | Length | Product Score |
|---|---|---|---|---|---|
| 1969935 (238) | 1798270 | 1103 | 99 | 259 | 91 |
|  | 2057694 | 765 | 100 | 234 | 65 |
|  | 1961765 | 600 | 100 | 245 | 50 |
|  | 473298 | 318 | 92 | 261 | 25 |
| 473298 (261) | 2057694 | 634 | 93 | 234 | 50 |
|  | 1961765 | 634 | 93 | 254 | 46 |
|  | 1969935 | 318 | 92 | 238 | 25 |
|  | 1798270 | 254 | 94 | 259 | 18 |

Alignments

1969935 ———————————————
1798270 ———————————————
2057694      ———————————————
1961765         ———————————————
473298             ———————————————

Creating a Master Cluster

Example: Cluster -12 (singleton), Cluster 2, and Cluster 1 all contain representative clones with PS ≥ 40 to Gene X.

Naming a Cluster

DATABASE FOR STORAGE AND ANALYSIS OF FULL-LENGTH SEQUENCES

CROSS-REFERENCE TO RELATED APPLICATIONS

This application is a continuation-in-part of:
1) U.S. application Ser. No. 08/289,822, filed Aug. 12, 1994, now abandoned;
2) U.S. application Ser. No. 08/581,240, filed Dec. 29, 1995, issued Nov. 24, 1998 as U.S. Pat. No. 5,840,870;
3) U.S. application Ser. No. 08/744,026, filed Nov. 5, 1996, issued Jul. 28, 1998 as U.S. Pat. No. 5,786,148;
4) U.S. application Ser. No. 08/786,999, filed Jan. 23, 1997, issued Apr. 6, 1999 as U.S. Pat. No. 5,892,016;
5) U.S. application Ser. No. 08/822,262, filed Mar. 20, 1997; issued Dec. 15, 1998 as U.S. Pat. No. 5,849,899;
6) U.S. application Ser. No. 08/951,750, filed Oct. 16, 1997; and
7) U.S. application Ser. No. 08/282,955, filed Jul. 29, 1994, now U.S. Pat. No. 6,114,114, which is a continuation-in-part of U.S. application Ser. No. 08/187,530, filed Jan. 27, 1994, issued Nov. 24, 1998 as U.S. Pat. No. 5,840,484, which is a continuation-in-part of:
   a) U.S. application Ser. No. 08/137,951, filed Oct. 14, 1993, now abandoned;
   b) U.S. application Ser. No. 08/179,873, filed Jan. 11, 1994; now abandoned; and
   c) U.S. application Ser. No. 08/100,523, filed Aug. 3, 1993, now abandoned, which is a continuation-in-part of U.S. application Ser. No. 07/977,780, filed Nov. 19, 1992, now abandoned, which is a continuation-in-part of U.S. application Ser. No. 07/916,491, filed Jul. 17, 1992, now abandoned.

which applications are incorporated herein by reference and to which applications we claim priority under 35 USC §120.

TECHNICAL FIELD

The present invention relates to the field of computer database technology as structurally applied to genetic data and corresponding cell information. More specifically, the structural relationship of the scientific information within a database and the application of this system to scientific and medical uses is disclosed.

BACKGROUND OF THE INVENTION

Genetic information, and the corresponding cellular and physiological information, is an extremely useful tool for a variety of uses. Comparative analysis of genetic information has been widely used in basic scientific studies, such as research into the molecular changes associated with disease, genetic differences in molecular evolution, and identification of individuals using forensic techniques. For instance, genetic information has been critical in determining the underlying molecular basis for a number of both heritable and sporadic cancers. These studies utilizing genetic information have allowed important advances in the medical field, providing mechanisms for prenatal diagnosis, identification of the presence or progression of disorders, and prognostic information on the aggressiveness of disease.

The ability to access genetic information quickly and efficiently is critical to the success of many of these scientific and medical uses. Currently, analysis of genetic and cellular information is generally done using molecular biology or biochemistry techniques in a laboratory setting. Although some of this research is computer aided, most analysis of such information is done by hand. Thus, the use of genetic and cellular information for scientific and medical purposes has practical limitations due to the quantities of human labor and time required for such analysis.

The state of computer technology governing the organization and use of genetic data has contributed to the limitations of the methods by which much scientific and medical analysis can be performed. Computerized tools for analyzing biological information are primarily targeted towards performing direct comparisons between sequences. Such techniques are very powerful in determining the relatedness of certain gene products with respect to other gene products, and may provide putative functions to novel gene products. Databases such as GenBank, for example, are widely used for such purposes. Databases such as GenBank are not, however, designed to efficiently perform more complex analysis such as abundance analysis between tissue types, subtractive analysis between samples of normal tissue and a tissue in a disease state, or similar comparative procedures. These tools to date have thus had a limited role in diagnostics, prognostics, and the optimization of patient treatment strategies.

Moreover, the majority of the databases used in biological and medical research are depository, i.e. sequences may be entered multiple times from different sources. Depository databases are not edited for accuracy; the mistakes that are present when the sequences are entered remain in the database files until the source of the sequence takes proactive steps either to remove or correct the information. For example GenBank, a widely used public gene-sequence database maintained by the National Center for Biotechnology Information, is a depository database. Sequences may be entered into GenBank from different researchers, and the information remains in the database until actively removed. An initial search that appears to show significant homology with a variety of sequences in GenBank may in fact be identifying multiple versions of the same gene sequence, with the each version merely having different sources and names. In a case where the sequences have minor variations from one another, depository databases do not provide any means by which to identify the correct sequence.

There is a need in the field for a computer-based system for efficiently analyzing and comparing genetic sequences and the corresponding cellular and physiological data. Such a system would greatly enhance the use of genetic information in the fields of medicine and biology. This would be especially beneficial in the area of patient care and treatment.

BRIEF DESCRIPTION OF THE DRAWINGS

FIG. 1 is a flowchart illustrating the process of mRNA isolation used in generating raw sequence data.

FIG. 2 is a flowchart illustrating the process of cDNA library construction used in generating raw sequence data.

FIG. 3 is a chart depicting the different editing methods used during automated bioanalysis, including the target sequence feature and the outcome of the editing process on each target feature. The # in (S≧#) in the BLAST editing methods reflects the stringency of that particular BLAST search.

FIG. 4 illustrates the di-nucleotide distribution tables used to identify aberrant sequencing errors in automated bioanalysis.

FIG. 5 illustrates the programming algorithm used to match high scoring pairs (HSPs) of two sequences using the BLAST program in automated bioanalysis.

FIG. 6 shows the possible pair-wise alignments and other parameters used in determining homology for the formation of a cluster.

SUMMARY OF THE INVENTION

Figure 7:
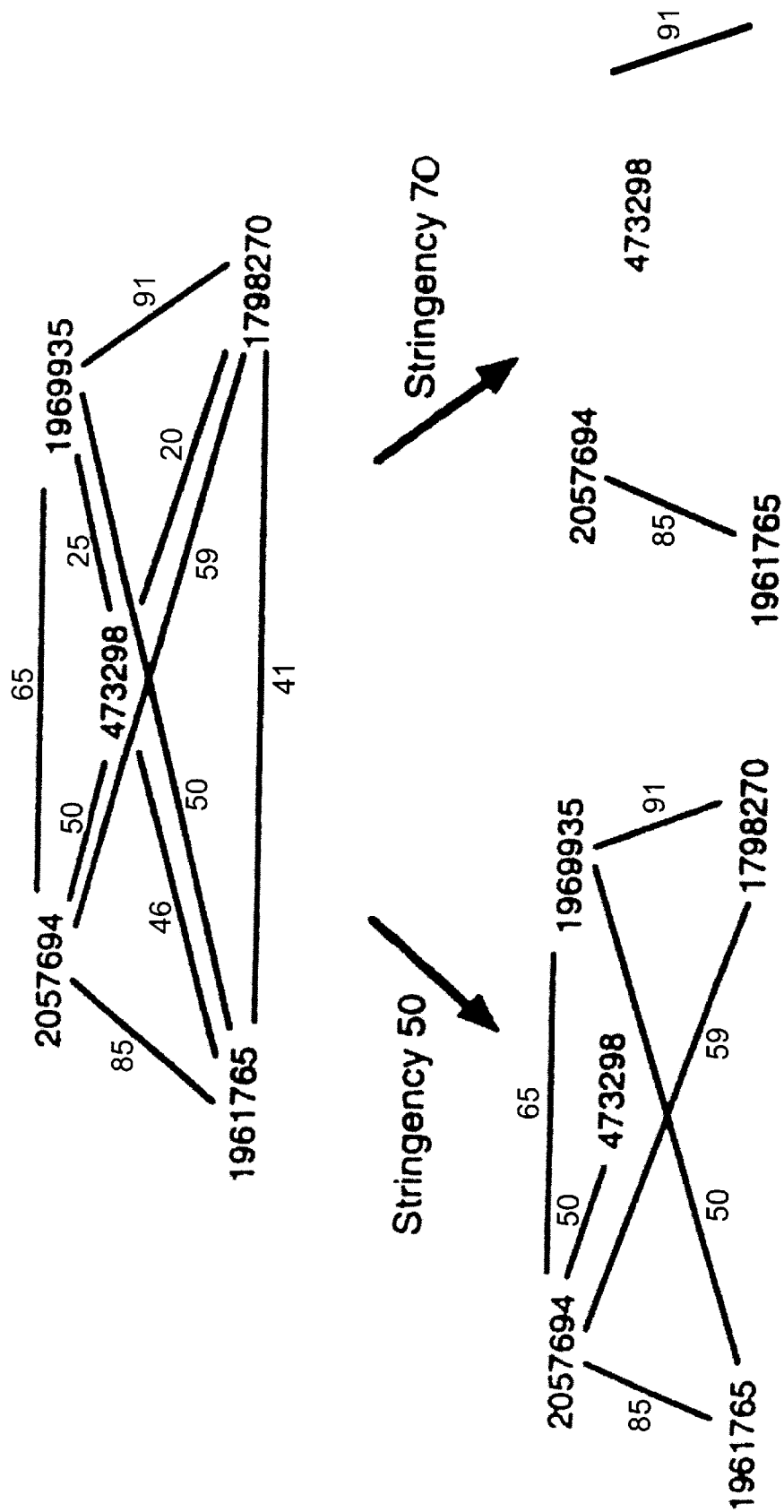
FIG. 7 illustrates the role of stringency in determining the sequences contained within a single cluster.

The present invention features a computerized storage and retrieval system for genetic information and related annotated information. The data of the system is stored in a relational database which interfaces with public databases to allow analysis both within an internal database and between information within that database and external public databases. The sequence data is edited before entry into the system, and is stored in a curated, functional clustering organization. The information associated with the data is stored in an expression database that is linked to the storage of the sequence data.

The invention features a relational database to store information where the database is comprised of a plurality of tables organized into categories.

One preferred embodiment of the database comprises cDNA sequences corresponding to transcripts that are differentially regulated in individuals with a particular disease (e.g. breast or prostate cancer) as compared to non-diseased individuals.

In another preferred embodiment of the invention, the sequences contained within the system are full-length cDNA sequences, preferably the full-length sequences SEQ ID NOS. 1–10.

An object of this invention is to relate the frequency of expression of all or any of SEQ ID. NOS. 1–10 in a test individual with the frequency of expression in a control group of individuals to determine differences.

It is an object of the invention to provide a system programmed with the ability to calculate significance values, perform gene expression analysis, generate transcript images, perform transcript image analysis, perform subtractive analysis, perform electronic Northern analysis, and perform electronic commonality analysis.

It is another object of the invention to allow the determination of information on tissue source, organ source, the pathology of the source, and patient information related to the sequences.

It is another object of the invention to allow access to information related to the processing and procedures of generating the sequences.

It is another object of the invention to provide a system suitable for use in transcript discovery.

It is another object of the invention to provide a system suitable for use in diagnosis, prognosis, and patient treatment determination.

It is an advantage of the invention that the sequences are edited by automated bioanalysis, thereby ensuring the integrity of the database.

It is another advantage of the invention that the sequences are arranged in a curated form to allow more efficient analysis of large quantities of sequence data.

The invention is also advantageous in that it allows comparison analysis of normal samples with diseased or potentially diseased sample.

Other aspects and potential uses of the invention will become apparent from the following detailed description and claims.

DETAILED DESCRIPTION OF THE INVENTION

Before the methods of the invention are described, it is to be understood that the invention is not limited to these particular methods. The terminology used herein is for the purpose of describing particular embodiments only, and is not intended to be limiting since the scope of the present invention will be limited only by the appended claims.

As used in this specification and the appended claims, the singular forms "a", "an", and "the" include plural references unless the context clearly dictates otherwise. Thus, for example, references to analysis of "a library" includes analysis to pooled sequence data of more than one library unless otherwise specified. References to "a method" may likewise include one or more methods as described herein and/or which will become apparent to those persons skilled in the art upon reading this disclosure.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated by reference for the purpose of disclosing and describing the particular information for which the publication was cited. The publications discussed are provided solely for their disclosure prior to the filing date of the present application. Nothing herein is to be construed as an admission that the invention is not entitled to antedate such disclosure by virtue of prior invention.

Definitions

"Stringency" as used herein means a combination of percent sequence identity and a length threshold between sequences, which is used to determine the relatedness of the sequences. Sequence identity for purposes of determining stringency is an exact match of the nucleotide base in a given position of the sequence. The chosen threshold of the stringency determines how related sequences must be to be considered a matched sequence. For example, a stringency of 50 means that a sequence is 50% identical to another sequence over a designated sequence length to be considered a match within the database, whereas a stringency of 70 means that the sequences must be 70% identical over a designated sequence length to be considered a match. A lower stringency results in a lower threshold for sequence matches. Stringency is used to determine levels of homology for purposes of searching databases.

A "representative sequence" as used herein means a sequence derived from a chosen representative clone or representative contig that is used to name a cluster. The representative clone or contig is the one with the highest matched score in a query with the GenBank or Blocks databases. If sequences of a cluster have no match in GenBank or Blocks, the representative sequence is derived from the clone with the lowest clone identification (ID) number. The clone ID of the representative clone is used to identify the cluster in gene expression analysis, transcript analysis, and comparative analysis.

A "cluster" as used herein means an organizational unit of cDNA sequences related by a given stringency. The clusters will vary depending on the chosen stringency; a lower stringency, such as 50, will have more sequences in each cluster, whereas a higher stringency, such as 70, will have fewer sequences in each cluster. Each cluster has a unique Cluster ID number based on the representative sequence within a given cluster stringency.

A "master cluster" as used herein means an organizational unit of cDNA sequences formed by joining clusters and single sequences with significant sequence identity matches to the same gene within a given stringency. The master cluster is named after the cluster or single sequence with the highest GenBank or Blocks match score to the gene.

"Low information sequences" are sequences that do not provide information useful in determining identity between sequences, i.e. sequences that may inhibit useful sequence match information by causing unrelated genes to match. An example of such a low information sequence is a low complexity sequence, such as a trinucleotide repeat contained within a gene. Although such a motif may be involved in gene function, it is not useful in determining nucleotide identity matches since it may result in numerous false positives. Another example of a low information sequence is a known repetitive element, such as a human Alu repeat. Since such low information sequences can cause insignificant matches between sequences, they are masked in the internal database for search purposes.

The term "curated" as used herein denotes a sequence organization whereby a representative sequence is chosen for use in analysis. The curated database of the preferred embodiment has sequences organized by clusters, super clusters, and projects. The projects are sequences derived from a particular tissue or sample. Each of these has a representative sequence that is used for analysis, both within the internal database and between databases.

A "relational" database as used herein means a database in which different tables and categories of the database are related to one another through at least one common attribute.

The term "internal database" as used herein refers to the relational database of the preferred embodiment. The internal database comprises full-length sequences that are stored in an annotated and curated organization.

The term "external database" as used herein refers to publicly available databases that are not a relational part of the internal database, such as GenBank and Blocks.

A "representative population" of cDNA sequences as used herein means a number of isolated sequences sufficient to statistically sample the genes expressed within a sample or project.

The term "sample" as used herein can mean either a biological specimen (e.g., tissue, cell, or other biological matter) or a reference source of cDNA sequence (e.g., cDNAs obtained from a cDNA supplier). The biological specimen may be either a cultured cell line, or a specimen taken from an individual. Such specimens include, but are not limited to, blood, urine, sputum, ascites fluid, cerebrospinal fluid, and biopsy tissue.

A "project" as used herein is a group of related sequences that can be assembled based on sequence overlap to generate a longer contig.

A "contig" is a series of overlapping sequences with sufficient identity to create a longer contiguous sequence.

The term "product score" as used herein is a score reflecting the percent identity between two sequences divided by the percent of the nucleotide overlap of the identity. This score may be used in determining homology between sequences and in determining cluster and master cluster arrangements.

The term "automated bioanalysis" refers to a procedure for preparing sequences for storage and use within the internal database of the preferred embodiment. Automated bioanalysis may include steps such as sequence editing, sequence masking, clipping portions of sequences, and removal of cloning and sequencing artifacts. It also includes functional arrangement of the sequences, such as clustering and master clustering, and transcript extension and expansion.

The term "transcript discovery" as used herein refers to the identification of a novel sequence using the invention as disclosed herein. This novel transcript may correspond to a novel gene, or to a novel variant transcript of a known gene. This transcript discovery may occur in automated bioanalysis (e.g. during transcript expansion) or during one of the comparison methods using the disclosed invention.

Generation of Raw Sequence Data

Raw sequence data is the unedited sequence information obtained directly from the sequencing of isolated DNA. Sequence data can be obtained through a variety of methods, including acquisition of sequence data from external sources. cDNA libraries are suitable sources for cDNA sequence information for the database of the preferred embodiment. cDNA libraries used for generating raw sequence data may be obtained from external sources or generated from a biological sample. The preferred method for generating raw sequence data from a biological sample includes the steps of: tissue preparation, RNA isolation, cDNA library construction, and template preparation and sequencing.

Tissue Preparation

Biological samples may be obtained from a variety of sources, including, but not limited to, blood, urine, sputum, ascites fluid, cerebrospinal fluid, and biopsy tissue. Since the time between tissue acquisition and preparation is critical for the success of the production of a fully-complex cDNA library (due to the typically short-lived and unstable life of RNA), the tissue samples are preferably prepared promptly. Preferably, 5 to 10 grams of tissue are collected. Not all of this material will be used in library production; a portion is stored in the event that the initial library construction fails. Preferably, current techniques that require only 2 grams of tissue are used.

Tissue libraries of the internal database of the preferred embodiment can be constructed from whole tissues, tissue sections, or specific cell populations. For example, a library may be constructed from a liver biopsy, or a section of a tumorous growth. A protocol for processing such a solid tissue sample may be: collecting 5–10 grams of solid tissue at the time of biopsy; within 15 minutes of collection, flash-freezing the tissue in liquid nitrogen; and storing the tissue at −70° C. until RNA isolation.

A library may also be generated from an isolated population of cells, such as lymphocytes. These cells may be isolated by a number of methods well known to those in the art. For example lymphocytes, due to their larger size and mass, can be isolated away from other cell population within a blood sample by centrifugation procedures. The isolated cell population can then be flash frozen at −70° C., and stored until RNA isolation.

Of particular interest is the construction of cDNA libraries from sources associated with certain disease states, including potentially malignant tissues. Tissues from healthy individuals, individuals with intermediate (e.g. hyperplasia) stages of the disease, and individuals with the advanced stages of the disease are all desirable for use in generating sequences for the database of the preferred embodiment.

RNA Isolation

Another step in cDNA library production is the extraction of RNA for use as template molecules. Total RNA can be isolated using any number of methods well known in the art. A preferred method is illustrated in FIG. 1. This method uses Trizol™, a monophasic solution of phenol and guanadine isothiocyanate. The sample is homogenized in this reagent, which maintains the integrity of the RNA while disrupting the cells and dissolving cell components. This step is followed by the addition of chloroform and centrifugation, and total RNA is recovered by precipitation with isopropanol. At this point, an optical density measurement is taken to assess the quantity of total RNA isolated, and an aliquot is run on an electrophoresis gel to assess the quality and integrity of the total RNA. The samples can then be stored until needed at −80° C.

To obtain cleaner total RNA, each sample is treated with DNAse and acid phenol, followed by precipitation and washing. The RNA is tested for the presence of genomic DNA contaminants. This pure total RNA is then subjected to selection for messenger RNA (mRNA). Preferred methods include an oligo-d(T) based affinity column, or Oligotex™ latex microspheres. The quality of the mRNA is tested, and the sample is then ready for cDNA library construction.

cDNA Library Construction

Once mRNA is isolated, it is used as template for the creation of a cDNA library (FIG. 2). The initial transcription of the RNA into single-stranded cDNA is termed first strand synthesis. First strand synthesis is initiated either with a poly-d(T) primer that is complementary to the poly-A stretch at the 3' end of most transcripts or a selected set of random primers. These primers may have engineered restriction sites for cloning purposes. Reverse transcriptase is used as the enzyme for production of first strands according to methods well known in the art. Second-strand synthesis is based on the method developed by Gubler and Hoffman (1983), and involves a 5' to 3' duplication of the second strand using a DNA polymerase such as Klenow. The end product from this initial stage of synthesis is a linear double-stranded cDNA with engineered restriction sites at both the 5' end and the 3' end.

The double-stranded cDNA is cloned into a vector by blunting the ends of the cDNA with T4 or Pfu DNA polymerase, and ligating an oligonucleotide adaptor encoding a restriction enzyme recognition site to the blunted ends. The cDNA can then be directionally cloned by a double digestion with a restriction enzyme that recognizes the site in the primer, and the restriction enzyme that recognizes the site in the adaptor. The cDNA is ligated into a plasmid vector system and introduced into cells for propagation, preferably into bacterial cells, e.g. *E. Coli*. Alternatively, the cDNA can be cloned into a bacteriophage vector system, e.g. a λgt11-based vector system.

After cloning, the DNA libraries may be normalized or amplified if desired. Normalization of a cDNA library involves removing multiple clones containing the same sequence in order to produce a library with more varied sequences. This process can be carried out by a number of methods well known in the art (see e.g. Bonaldo et. al (1996) Genome Res. 6: 791–806). Since most of the highly expressed sequences have been removed, normalized libraries are useful for gene discovery. Normalized libraries are not, however, an accurate representation of cellular transcripts, and are not useful for transcript imaging.

Amplification of libraries is often done to establish a permanent supply of a particular library. Amplification can be carried out by any number of methods known in the field (see, e.g., Sambrook et. al. (1989) *Molecular Cloning: A Laboratory Manual*). Amplification can affect the total sequence population contained within the library, since certain clones are preferentially amplified due to inherent biases in amplification procedures. Procedures (such as transcript imaging) with amplified libraries may thus be skewed, and as such are not necessarily an accurate representation of what would be present in a primary, unamplified library.

Template Preparation and Sequencing

Once cDNA libraries are constructed, the plasmids containing the cDNA sequences are purified to be used as templates for sequencing. Methods for preparation of sequence templates and sequencing are well known in the art (see, e.g., Sambrook et. al. (1989) *Molecular Cloning: A Laboratory Manual*). For example, where the cDNA is cloned and propagated in a bacterial host cell, bacterial colonies containing the plasmids are incubated overnight, and an automated colony picker is used to select individual colonies into a 96-well plate. After an overnight incubation, bacterial cells are lysed, and the plasmid DNA is purified from the colonies and resuspended in water. Alternatively, where the cDNA is cloned into a bacteriophage vector, bacterial cells are infected with the library-containing phage, the cDNA is extracted and purified from selected plaques, and the DNA is resuspended in water.

Prior to the sequencing reaction, the concentration of DNA should be determined for each sample. This may be done using mass spectroscopy, approximation from gel electrophoresis comparison, or a number of different methods known in the art. Preferably, a small amount of fluorescent dye is incorporated into a small aliquot of each DNA sample, and a fluorometer is used to determine the quantity of DNA. If the sample contains an acceptable concentration of DNA, the template is prepared for sequencing. An aliquot is saved and stored for archival purposes.

Sequencing can be performed by a variety of methods well known in the art. Preferably, the sequencing methodology uses fluorescently-labeled primers in the sequencing reaction. For example, templates can be labeled with Amersham's Energy Transfer primers. These primers have a fluorescently dyed tag which corresponds to each of the four nucleotides. Each tag fluoresces a different color when scanned by a laser beam in the sequencers. The information from the laser scan is converted into the letters representing the appropriate nucleotides (A, C, T, and G) and stored in a computer file. Bases that cannot be read due to low noise, low sample concentrations, or faulty gel conditions are represented by Ns. Once a sequencing gel run is complete, each lane is analyzed to determine the quality and readability of each sequence.

Sequences of acceptable quality constitute raw sequence data. Once generated, this raw sequence data can then be subjected to automated bioanalysis, and entered into the internal database.

Automated Bioanalysis

Once raw sequence data is generated for clones from cDNA libraries, the sequences are preferably edited and annotated before entry into the internal database. This editing and annotation process is divided into two levels of processing: 1) screening ane editing raw data; and 2) annotating and organizing edited sequences. A third level of processing uses existing edited sequences to extend sequences and identify related sequences prior to annotation and storage. These collective levels of processing are termed automated bioanalysis.

The first level is comprised of a number of different editing screens aimed at removing sequence elements that will interfere with analysis and decrease a sequence's usefulness in the database. These screens may vary in order, but most preferably the screens are done in order of increasing search stringency (FIG. 3). Not all steps must be applied to all sequences. In addition, further editing screens may be used in this process, and as such the invention is not limited to the described editing procedures. Edited sequences may enter level two at this point, or proceed to level three before entering level 2.

The second level involves organization and annotation of sequences based on their similarity to each other and to identified sequences (e.g., in publically-available databases). Matches and identities are detected and recorded. If no significant identities can be detected, sequences can also be evaluated for patterns including functional motifs.

The third level involves the identification of additional transcript sequences for entry in the database. Sequences are compared to external databases to extend the sequence prior to entry into the database. In addition, sequences homologous to edited sequences are identified as novel sequences to expand the database holdings.

Level 1: Sequence Editing

Sequence editing allows comparisons made within the internal library and between sequences in the internal and external databases to provide more meaningful results. Elements with a portion of the cDNA sequence that is not useful in database searches (e.g., repeat elements) may have a high identity with another cDNA sequence, but the sequences themselves may not be related in any meaningful or informative way. Where database queries are based on random identity between sequences, such sequence elements can result in false matches which can interpretation of analysis and may be misleading. Thus, it is desirable to edit certain sequence elements from the raw sequences before storing them in the internal database.

During the first level of automated bioanalysis, raw sequences are subjected to editing analysis to remove unwanted sequence elements. The sequences pass through a series of screens that recognize common unwanted sequence elements, and these elements are either removed completely, clipped from the remaining desired sequence, or masked for the purposes of performing analytical comparisons with the desired sequence. These screens are designed to recognize and neutralize sequence elements including vector sequences, motifs such as poly-A tail sequences, cloning and sequencing artifacts, contaminating sequences (e.g., sequences not from the desired source), repetitive elements, mitochondrial sequences, and ribosomal RNA (FIG. 3). In the preferred embodiment, four separate screens are used in the editing process to identify and neutralize sequence elements that will hinder useful sequence analysis: 1) identification and removal of vector sequences, 2) identification and removal of non-informative motifs, 3) identification and removal of cloning and sequencing artifacts, and 4) identification and masking of low information sequences. These screens may be performed in varying order, but preferably in order of increasing stringency. The specific screens of the preferred embodiment will now be discussed in further detail.

Detection of Vector Sequences

Detection of vector sequences is performed to remove vector sequence that are remnants of the cloning process. Vector sequences remaining in the sequence may cause a cDNA sequence to match with other sequences with no relation to the coding portion of the gene. Generally, this is accomplished by comparing the raw cDNA sequence with known vector sequences and detecting sequences identical to the known vector sequences.

To identify vector sequences, a dynamic programming algorithm is used to optimally align two sequences. Such programs identify homology between nucleic acid species, ribonucleic acid species, a combination of the two, or deduced amino acid species. The anchored dynamic programming algorithm for sequence alignment is the preferred algorithm for this purpose, as it is the most accurate and sensitive method for detecting identity between sequences using linear gap scores. This algorithm forces an alignment of sequences at both vector boundaries within the cloned sequence. All sequences recognized as vector are clipped from the sequence. Every raw sequence should contain some vector sequence at least one end of the sequence; if no vector sequence is detected at this step, the sequence is removed from further analysis under the presumption that it is a containment.

Identification and Removal of Non-informative Search Motifs

This screen is designed to remove common sequence motifs that may otherwise cause unrelated sequences to match upon comparison analysis. One example of such a motif a linker adaptor, which is a sequence used in the cloning process. Another example of a motif that is removed for sequence search purposes is a poly-A tail.

An algorithm is used to match what are termed "regular expressions" that represent such motifs in the nucleotide sequence. Regular expressions are based in part on identity, but also factor in possible deviations that would still result in such a motif, and would possibly result in an identity match in sequence analysis in the database. Thus, using a regular expression sequence algorithm allows identification of functional motifs, even in the absence of direct nucleotide identity.

Motif matching based on regular expressions is an efficient method for quickly detecting specific nucleotide character patterns in a sequence. Relaxed versions of motif matching allow a selected number of nucleotide identity mismatches, i.e. unmatched nucleotide base pairs, in the alignment of sequences encoding unwanted structural motifs. Constraints on nucleotide position in the regular expression sequence are used to determine the presence of certain motifs. For example, the constraints used to detect a poly-A and linker sequence were: Poly-A-"AA[ANT]AA [AAN]*$" These allow the detection of poly-A sequences in different mRNA species despite some deviation in the nucleotide sequence. Sequences encoding structural motifs that are uninformative for search purposes are removed (e.g. linker adaptor sequences) or masked (e.g. poly-A sequences) in the edited sequence.

Identification and Removal of Cloning and Sequencing Artifacts

This screen identifies and removes sequences created through error in the generation of raw sequence data. This is accomplished by the comparison of dinucleotide distributions between the sequence being edited and average levels of dinucleotide distributions. A dinucleotide distribution is the relative frequency with which a particular set of two nucleotides, e.g. "CG", will occur within a given sequence. These dinucleotide distributions, which are generated through the Nearest Neighbor analysis statistical program, can be used to detect sequences that by virtue of their composition were likely to be sequencing artifacts.

In this process, a table of dinucleotide distribution is formed for each sequence, and compared to the expected distribution calculated from the individual nucleotide composition (FIG. 4). A chi-squared statistical program is used to compare the actual dinucleotide distribution to the expected dinucleotide distribution. The expected dinucleotide distribution is generally calculated as if dinucleotides were independently generated (i.e. equal likelihood of each dinucleotide). Actual distributions that vary widely from the expected distribution are suspect for sequencing artifacts. The range of dinucleotide distributions may vary depending on the nature of the sequence, and known motifs with the sequence. Sequences having dinucleotide distribution that varies by a selected degree from the expected dinucleotide distribution are removed from further analysis in the database.

One aim of this editing step is to remove contaminating sequences from the host cell in which the clone containing the DNA of interest is grown. Sequences from host cells such as *E. Coli* are recognized by their nucleotide distribution and/or by homology searches done using BLAST searches. Sequences that are thus identified are removed from further analysis.

Identification and Masking of Low Information Sequences

This screen identifies sequences that provide low information in a search, such as non-informative repetitive elements. Low information sequences, although not necessarily informative in comparative analysis, are a part of the actual sequence, and thus are masked in the edited sequence instead of removed so that the low information sequence can be obtained in the database if necessary. These sequences are masked by substituting an N for the actual nucleotide (i.e. G, A, T, or C). This masks the low information sequences for search purposes but preserves the spacing of the DNA molecule. The actual sequences corresponding to the masked sequences are stored for informational purposes.

For example, a low complexity sequence such as a di- or tri-nucleotide repeat may cause sequences to match in a search query without the match producing any useful identity information between the two coding regions of the two sequences. These sequences should not be removed completely, however, because they may provide information regarding the function of the predicted protein product. Similarly, more dispersed repetitive elements such as human Alu repeats may cause uninformative matches between two sequences. The masking procedure is important since many search algorithms are concerned only with the number of base matches in an alignment, without considering any complexity or positioning of the matching sequences within an analyzed sequence.

Local alignment tools allow the matching of a query sequence to sequences stored in a database. Preferably, the Basic Local Alignment Search Tool (BLAST), the most commonly used database search tool, is used for detecting ungapped subsequences in a database that match a given query sequence. (Altshul et. al.(1990) J. Mol. Biol. 215, 403–10; Karlin and Altshul (1993) PNAS 87: 2264–8). The algorithm upon which BLAST is based, and which is described in more detail in the incorporated reference, is shown in FIG. 5. A series of BLAST comparisons is performed to identify sequence elements that may impede analysis in the database. Sequence elements determined to be of low information or low complexity are thus masked.

Level 2: Annotation and Organization

Sequence Annotation: Experimental and Source Data

Edited sequences are entered into the internal database of the preferred embodiment, which is a relational database. The sequences are stored relationally with annotated information relevant to the sequences, such as experimental data regarding the biological source tissue, information about the pathology of the biological source of the sequence, information on the patient from which the tissue was derived, experimental procedures used to generate raw sequence data from the biological source, and methods used in editing the sequence. The nature of the information and the organization of this annotated information relative to the sequences is described in detail below.

Annotation: Functional Identification

Edited sequences are first analyzed against a basic informative database, preferably the GenPept database. Matches receive a score (e.g. a P-value) that indicates the probability that the match between the query sequence and the GenPept sequence are due to random chance. Matches also receive a BLAST score that indicates the quality of the alignment between the matched sequences. The threshold can be set to determine the stringency of the match, and to prevent as many false positive matches as possible. Although this threshold may vary, preferably the threshold set is a P-value of 10—10, and a BLAST score equal to or above 100. If the comparison produces a match that exceeds the determined threshold, the sequence is annotated with the appropriate match information and further comparisons are halted. If there is more than one match, information pertaining to the most significant match is used.

If no significant matches were found in GenPept, the sequence is compared against the GenBank Primate (gbpri) database. Annotation determination is based on percent identity and BLAST score threshold. As with GenPept, this can vary according to the desired stringency. Preferably, the percent identity must be 80 and the BLAST score above 250. If this search fails to produce a significant match, the comparison is repeated with the GenBank Rodent (gbrod) database, with a preferable threshold of 75% identity and a minimum BLAST score of 250. If no match is found in gbrod, the sequence is annotated to indicate that no match was detected and to indicate the databases searched.

Following this procedure, sequences may follow one of at least two potential routes: they may be organized as functional cluster arrangement for storage in the database structure, or they may proceed to level 3 analysis, and entering the clustering organization after level 3 processing.

Organization: The formation of clusters

Following the screening procedures, sequences with a significant amount of identity (as determined by BLAST) are organized into a single linkage cluster using pair-wise alignment analysis (FIG. 6; see also Example 2). Percent identity and the length of the region exhibiting this identity are used to determine a product score between a sequence and other match sequences identified in the BLAST search. A higher product score reflects a higher relative similarity between sequences. Stringency in the BLAST searches can be predetermined, and may determine the number of overall clusters created in a comparison of sequences. The range of stringency can be between 50% and 100% with a predetermined minimum overlap of 10–300 nucleotides, but most preferably is 95% over at least 30 nucleotides. The higher stringency results in fewer false positives within the cluster arrangement. At a lower stringency, single-linkage analysis may create a single large linkage cluster, whereas a higher stringency would break some of the single linkages, leading to multiple smaller clusters (FIG. 7). Thus, higher stringencies require higher product scores to link sequences in a cluster.

Creating and Identifying Clusters and Master Clusters

Each sequence in the database can be grouped into one of any several different relationships for storage in the database. One way of defining such relationships is a process termed "clustering" The clustering process depends on numerical thresholds, most of which are an iteration of scoring output from BLAST comparisons. The BLAST scoring output is related to two important scoring methods: product score and log likelihood. Since the database of the present invention is curated, a single representative sequence for each cluster and master cluster is selected.

Choosing a representative sequence

For a given tissue or project, a sequence is chosen to be the representative sequence for the project. This selection is based on sequence status, and the quality of the sequences available as representative sequences. The sequence may be one that is assembled from a number of different clones. More preferably, the representative sequence is from a clone that has a 5' complete sequence. Most preferably, the representative sequence is a complete, full length cDNA sequence. In short, if a full-length sequence is available, it becomes the representative sequence. If none of these sequences exist, the first sequence identified for a clone is the representative sequence. If more than one sequence falls into a single category, the representative sequence will be contained in the clone for which the most information is known.

Determining clusters

The product score, derived from the BLAST score, serves two purposes: it assigns cluster membership at separate stringencies, and it determines the quality of the match between two sequences, for example between an internal sequences and an external public sequence database for purposes of annotation. Stringencies are predetermined in the internal database, and may be as low as 25%, preferably at least 50%, more preferably at least 70%. These stringency ranges directly reflect the percent identity between sequences in the clusters. In a preferred embodiment, stringencies used to determine clusters are between 70–95%. Sequences may be stored in the internal database in two different cluster stringencies.

Clusters are formed on the basis of single-linkage relationships, i.e., the relationship in the cluster need only be based on one single sequence within that cluster. If two sequences do not physically overlap at a specified stringency, but they both overlap a third sequence, then the use of single-linkage association can appropriately place all three sequences in the same cluster. This allows sequences that do not physically overlap to be part of the same cluster (see FIG. 8). A sequence that has no overlap to other database clones at a given stringency is not clustered and labeled as a "singleton." A sequence with no match in the public databases is referred to as unique.

Figure 9:
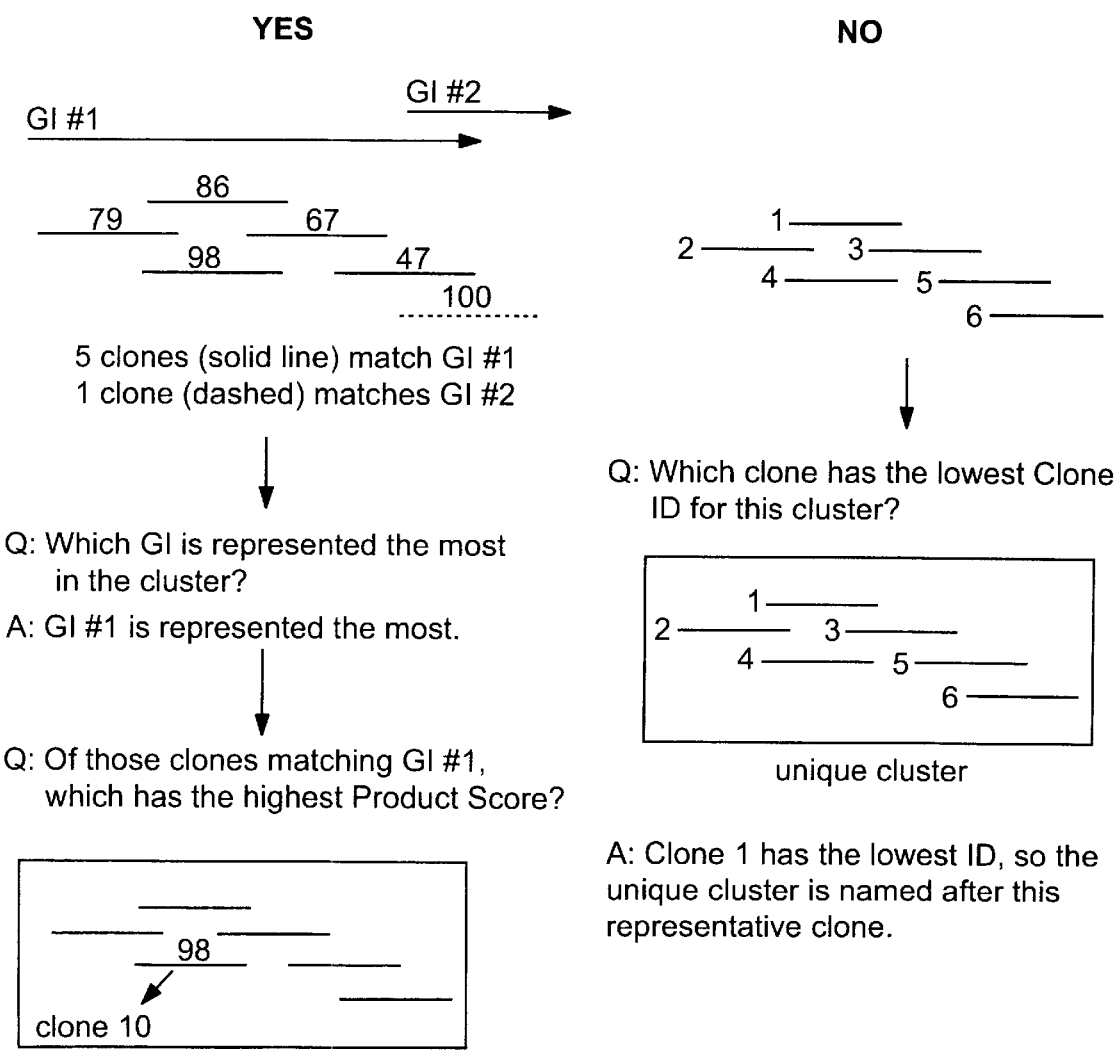
FIG. 9 depicts the use of different parameters in the naming of a cluster. Clusters are named after the clone with the highest Product Score for the most common GI represented in the cluster.

Sequences having identity within a selected stringency are organized into clusters, and assigned an arbitrary, unique cluster ID number. The cluster ID for a particular cluster may change between stringencies. A sequence can only belong to a single cluster at a given stringency, and thus will retain the same cluster ID number for all operations. Preferably, the cluster is named after the representative sequence., i.e. the sequence with the highest Product score for the most common GenBank Identifier (GI) (FIG. 9). The clustering process is dynamic, and the information changes as more sequences are added to the curated database.

Determining master clusters

Figure 8:
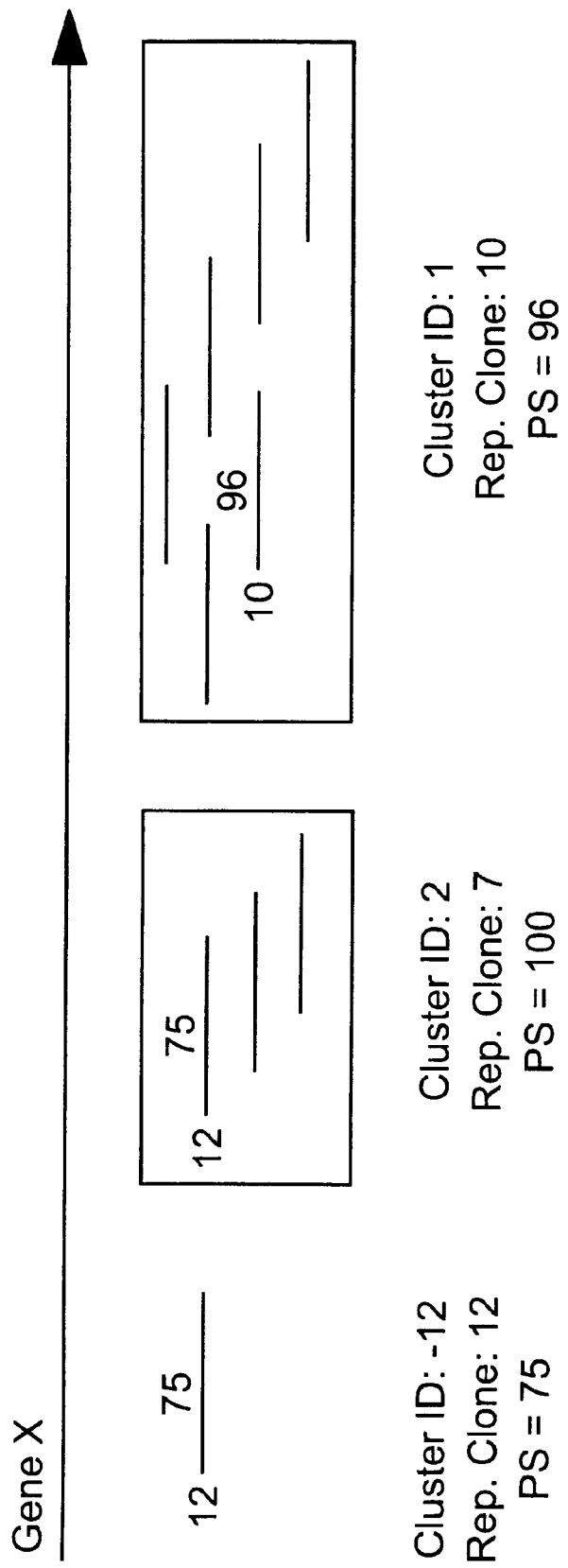
FIG. 8 depicts the process of creating a master cluster. Master clusters are formed by joining clusters and singletons that have representative clones with a significant Product Score to the same gene.

Once representative sequences have been chosen for all clusters, the curated database is used to form master clusters. Master clusters are formed by joining clusters and single sequences (singletons) that have representative sequences with significant matches (a Product score of 40 or more) to the same gene (FIG. 8). Preferably, this is accomplished using NCBI's Unigene Database, which indexes all sequences that match the same gene.

The representative sequence for the master cluster is the sequence that matches one of the indexed sequences with the highest Product score. The master cluster ID is identical to the cluster ID of the representative sequence, i.e. the master cluster inherits its representative sequence's cluster ID. Individual sequences retain their original cluster number and representative sequence within the master cluster. If a cluster does not meet the criteria for inclusion in a master cluster, it will be treated as if it were a master cluster consisting of one cluster.

Level 3: Transcript Extension and Expansion

Transcript extension cDNA sequences corresponding to full-length mRNA transcripts are preferable for use in the searches performed using the present invention. Known edited sequences can be expanded into longer, more complete, and preferably complete cDNA sequences using a transcript extension scheme. This scheme provides utilizes information in external databases to aid in the construction of a more complete representative sequence for use in the database. Edited sequences are used to find overlapping sequences in external databases, and these sequences can be pieced together to form a contig that more fully represents the transcript sequence. Sequences may be subjected to the extension scheme either prior to the clustering arrangement, or the sequences may be analyzed in the cluster unit.

In the transcript extension scheme, a single or representative sequence is compared against the available databases using the BLAST program. Sequences with a sufficient BLAST score and percent identity are grouped together. Preferably the BLAST score is >250, with a preferable percent identity greater than 90%. Overlapping sequences that meet this criteria are then assembled into a contig with the sequence used for the initial search. This can be accomplished using any of the assembly engines known in the art, and preferably Phrap engine (Phil Green, U Wash).

The contig containing the original sequence becomes the new representative sequence. The transcript extension scheme process is then repeated using the new representative sequence for comparison against available databases. This process is repeated until the sequence does not elongate any further. The new, extended sequence then proceeds through level 2 processing for annotation, clustering and storage.

Transcript Expansion

Another method for increasing the number of available sequences in the database is transcript expansion, which utilizes edited sequences to identify cDNA sequences corresponding to related, but not identical, transcripts. In transcript expansion, an individual or representative sequence is used to identify other transcripts that are homologous to the original sequence. By using a lower stringency threshold than clustering or transcript extension, sequences that are similar but not identical are identified; these new sequences may identify sequences from novel genes or novel splice variants of known genes.

A sequence is compared against the available databases using the BLAST program, and sequences above a lowered threshold are retained. Sequences identified in this manner are compiled as a list of potential novel homologous genes. The searches are designed to tolerate false positive matches in order to identify genes with significant similarity to the original sequence. Identified sequences are then compared against the available databases to identify other sequences with significant similarity. This is repeated until no further sequences are obtained.

The identified potential novel homologous sequences are then assembled into contigs, preferably using the Phrap assembly engine. These newly identified sequences are assembled at a higher stringency, and subjected to the same annotation and organizational structure as the original or clustered sequences. The sequence corresponding to the contig of each novel transcript is the representative sequence for that transcript. These new sequences are then sent to level 2 for annotation, clustering and storage.

Database Organization

The database of the present system utilizes the capabilities of modern computers by storing genetic information in association with a large amount of related information. In a preferred embodiment, the information on essentially all the steps of obtaining tissue, extracting transcripts, cloning, and identifying cDNA sequences is stored in various relational tables. The database can also allow a user to access information pertinent to the cDNA sequences, such as experimental processing information and medical history of the individual from which the biological sample was derived.

Figure 10:
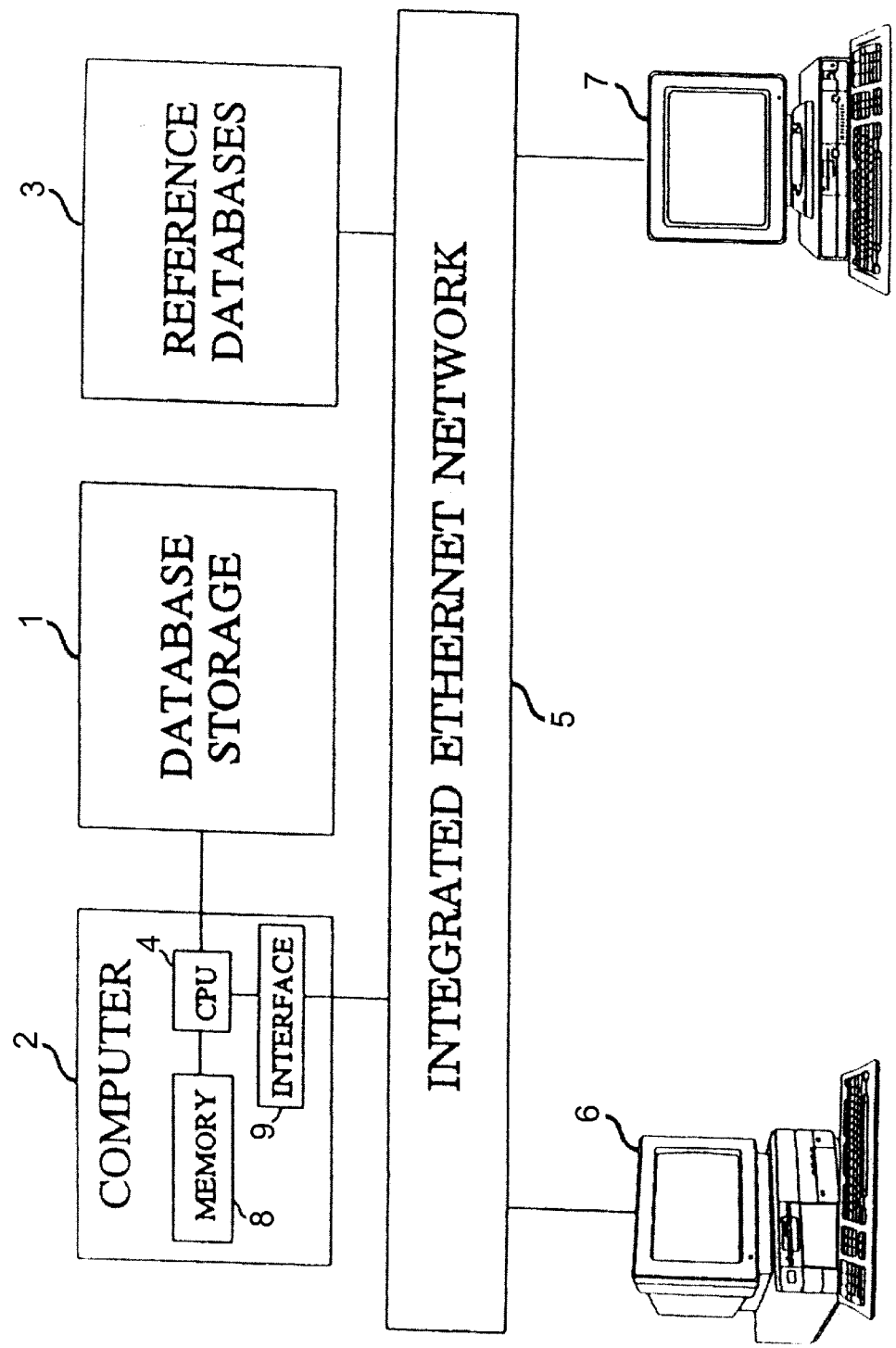
FIG. 10 depicts the structural relationship of the relational database system of the preferred embodiment of the present invention.

Both sequences and information annotating the sequences are stored in a relational database. Data is stored in the relational database in a functional arrangement that allows the user to store, track, and manipulate the cDNA sequences and annotated information. Users can access one or more relational databases via an integrated network, e.g. an Ethernet network. The workstations are typically computers, preferably personal computers, that include data entry means, output devices, display, CPU, memory (RAM and ROM) and interfaces to the network (FIG. 10).

Figure 11A:
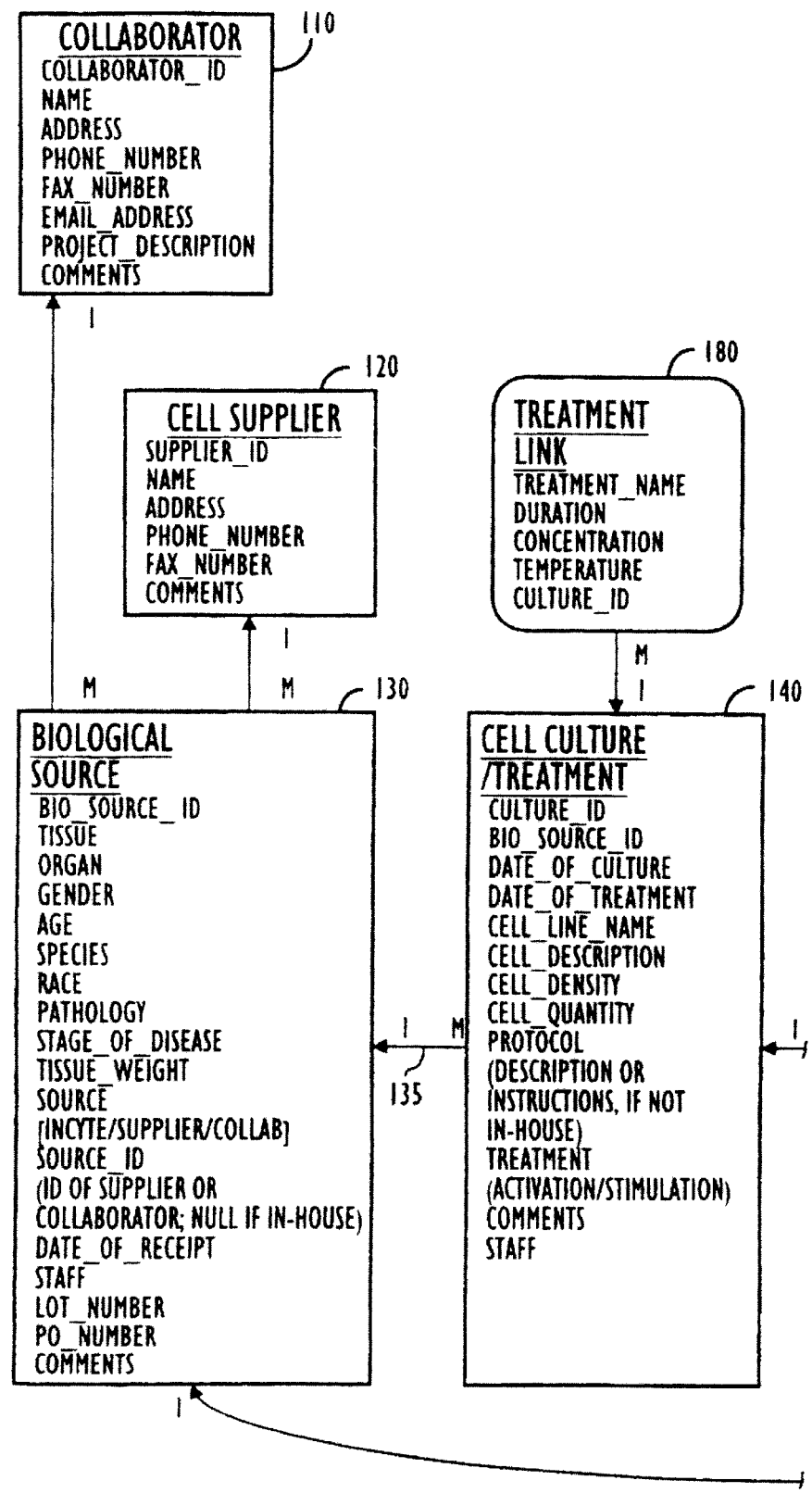
FIGS. 11–16 illustrate categories of annotated data as organized in the relational database. Each of the categories consists of a plurality of tables, each table containing information on different attributes related to a cDNA sequence. Each of the tables shares at least one attribute with another table in the category, and at least one attribute within the category is shared with another category.
Figure 11B:
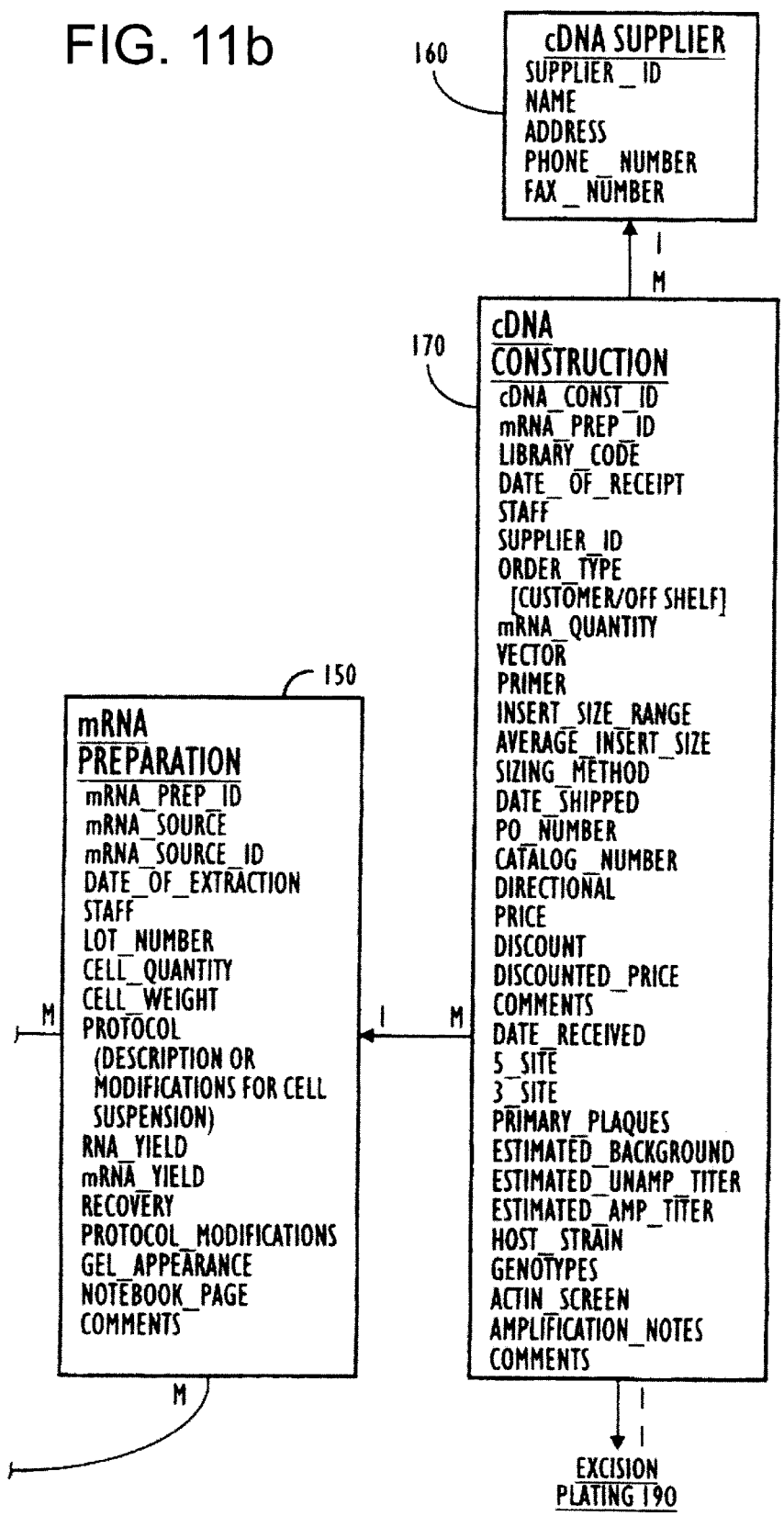
Figure 12:
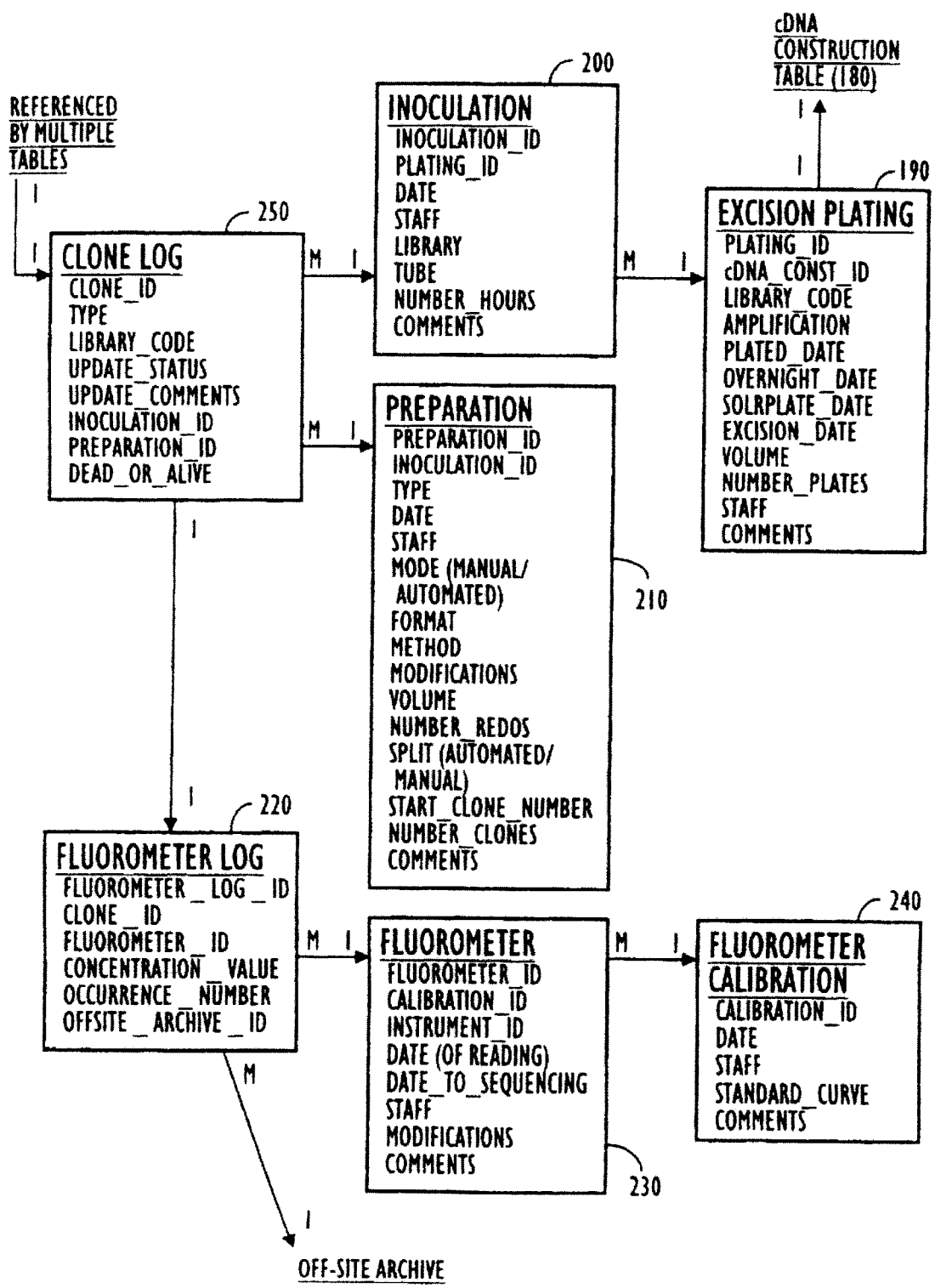

In the preferred embodiment of the present invention the database is stored at a file server connected to network, as schematically represented in FIG. 11. Computers 6, 7 are linked, via an integrated network 5, to a computer 2 that grants access to the storage unit 1 of the internal database of the present invention. The access computer 2 preferably includes CPU 4, a memory means 8, interfaces to the network 9, and input and output devices. Reference databases illustrate sources of data which, for example, may be searched during use of the database.

Organization of Sequences and Annotation Information

Sequences and associated annotations pertaining to each sequence in the database are entered and stored in an expression database. The annotations, assigned through the automated bioanalysis, may contain information on the cells and tissues where the genes corresponding to the isolated cDNA sequences are expressed, identity to known genes, probable gene product function, and preparation techniques. The sequences from cDNA libraries are preferably organized by tissue category. Exemplary tissue categories include, but are not limited to: cardiovascular, endothelial, fetal, endocrine, gastrointestinal, hematopoetic/immune, hepatic, musculoskeletal, neural, pancreatic, female reproductive, male reproductive, respiratory, sensory, and urologic. Information about the production of clones produced in a cDNA library from a particular tissue is annotated with the sequences.

Preferably two formats for presenting information can be selected by a user. The first is a short description, which appears in the tissue category list, to help in initial identification of a library. A standard short format preferably includes tissue name, disease state (if applicable), patient age/gender, and special information. The second format is a longer format, with more detailed, descriptive information on each of the categories of the short format. By clicking on the short format, additional information is made available in the long format. Tissue information may also include non-confidential patient information, tissue pathology, library preparation techniques, and information about other related libraries available in the database.

Figure 16:
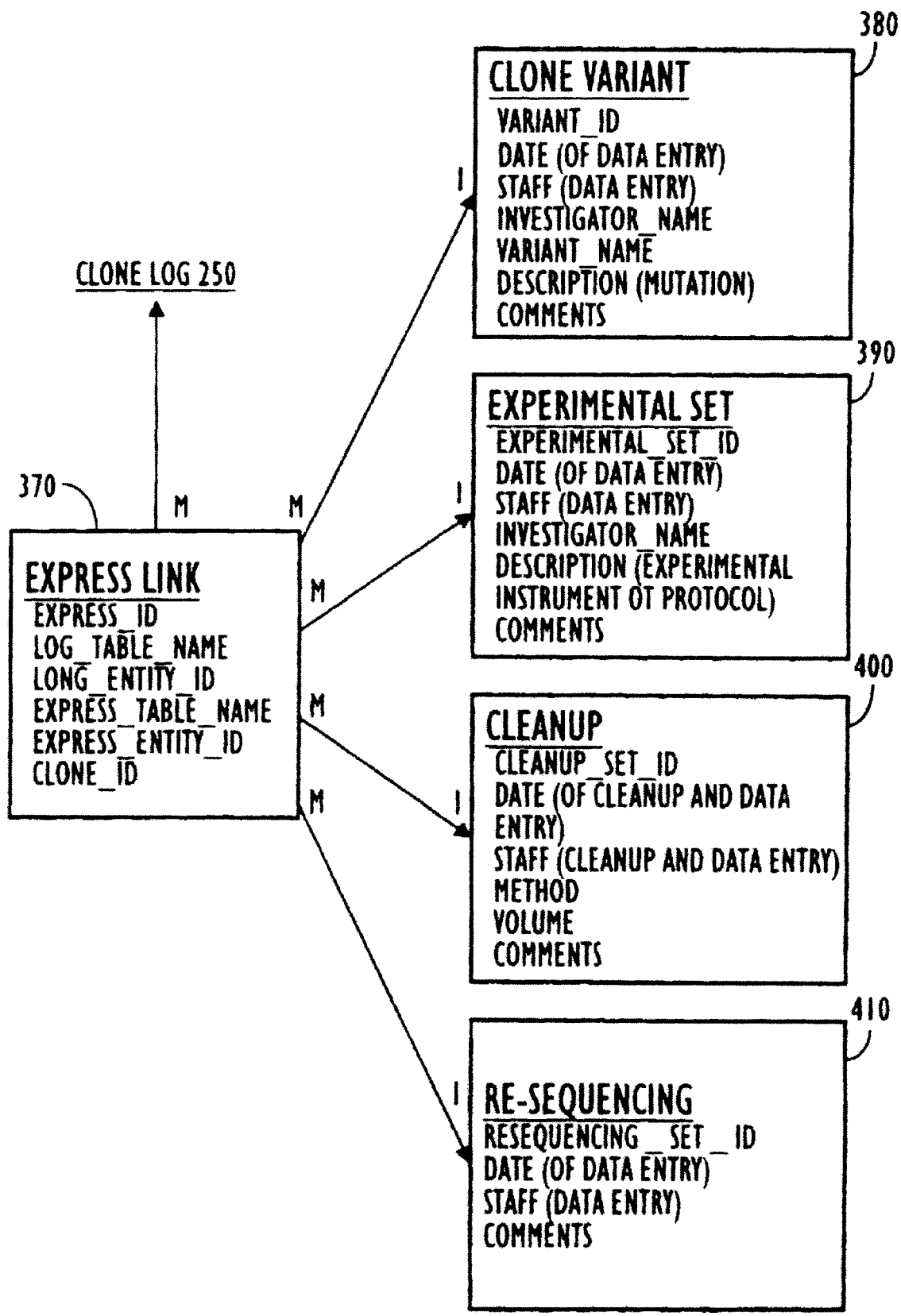

FIGS. 11–16 illustrate different categories within the expression database of one preferred embodiment. The sequence-related information is organized as a plurality of tables in the database. Preferably, the database contains storage categories for the areas of library preparation (FIG. 11), clone preparation (FIG. 12), sequencing (FIG. 13), sequencing equipment (FIG. 14), sequencing reagents (FIG. 15), and express sets (FIG. 16). Exemplary fields, or attributes, within each table are depicted in each box.

The database is relational in that each table contains at least one overlapping attribute with another table (i.e., common attribute), both within a category and between categories. For example, compare the table indicated as "Biological Source" 130 with the table indicated as "Cell Culture/Treatment," 140 both in FIG. 12. In these two tables the common attribute is bio_source_ID. In comparing the table indicated as "cDNA Construction" 170 in the Library Preparation category (FIG. 11) with the table indicated as "Excision Plating" 190 in the Clone Preparation category (FIG. 12), the common attribute is cDNA_const_ID.

The library preparation category (FIG. 11) contains information corresponding to the sample used to generate the cDNA sequences stored in the database. Both the physical information (e.g. supplier or collaborator) and physiological information (e.g. medical and biological information relating to the sample) are stored in the library preparation category. The physical history of the sample for source tissues from which cDNA must be produced are stored in the collaborator 110 and cell supplier 120 tables. The physical history of the sample for cDNAs produced from an outside supplier are retained in the cDNA supplier table 160. Physiological history of the sample are stored in the tables biological source 130, and cell culture/treatment 140, and treatment link 180. Methods and measurements pertaining to the construction of cDNA from the sample are stored in the tables mRNA Preparation 150 and cDNA Construction 170. The library preparation category is related to the clone preparation category by the attribute cDNA_const_ID, found in the Excision Plating table 190 and the cDNA Construction table 170.

The clone preparation category (FIG. 12) contains archival information about the preparation of clones. This category of the database contains information regarding clone preparation data that is obtained during the cloning process and includes information relating to excision, inoculation, and preparation. The inoculation table 200 contains information describing the process of growing the clones containing the cDNA sequences. Fluorimetry procedures to determine cDNA purity and concentration are stored within the fluorometer table 230 and the fluorometer log table 220. The preparation table 210 contains information on methods used in the growing and harvesting of clones after processing with the fluorometer. Data on the excision process, which is the removal of the cDNA fragment from the vector, is stored in the excision plating table 190. The clone log 250 combines information regarding the cloning process.

Figure 13:
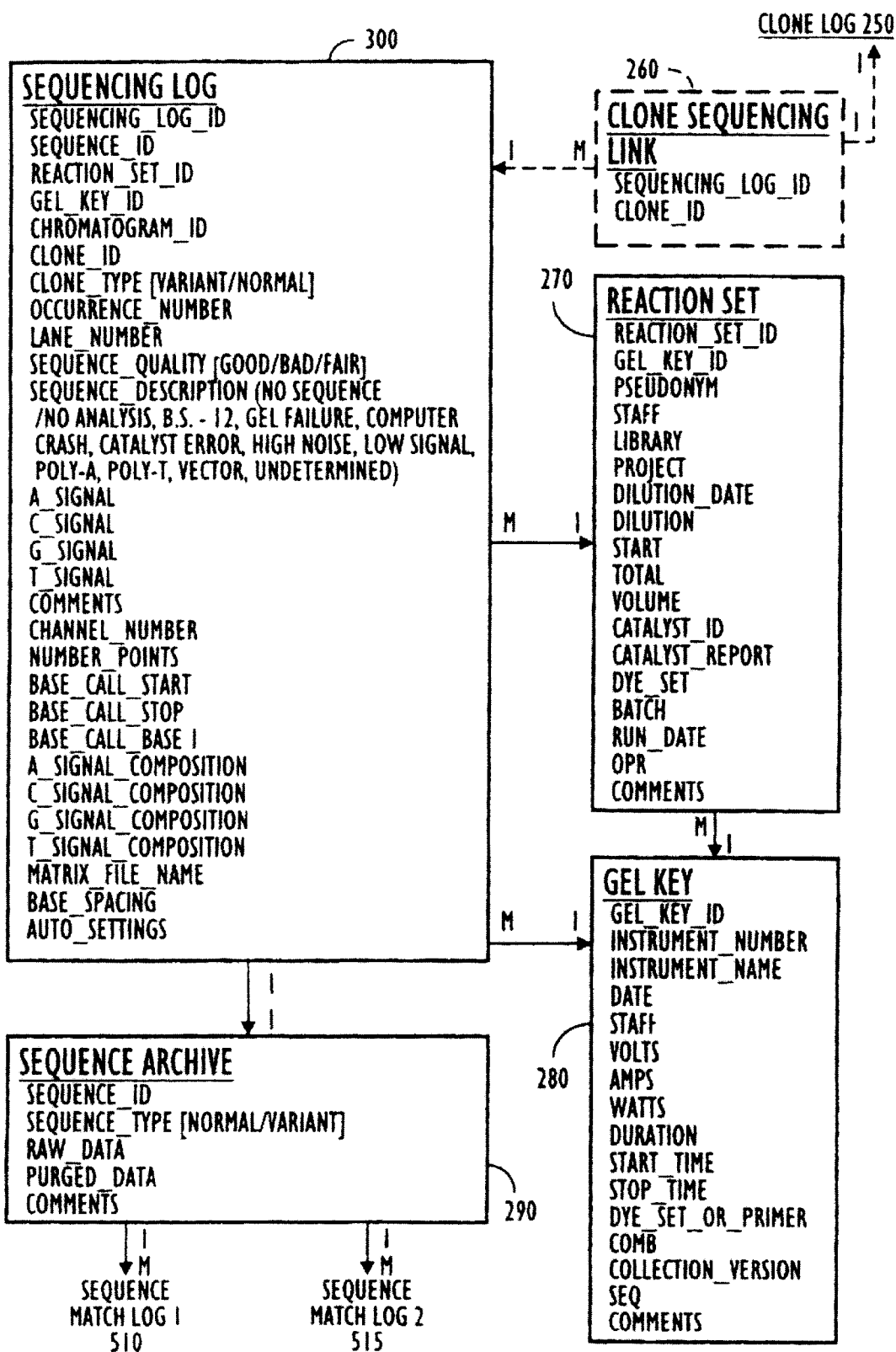
Figure 14:
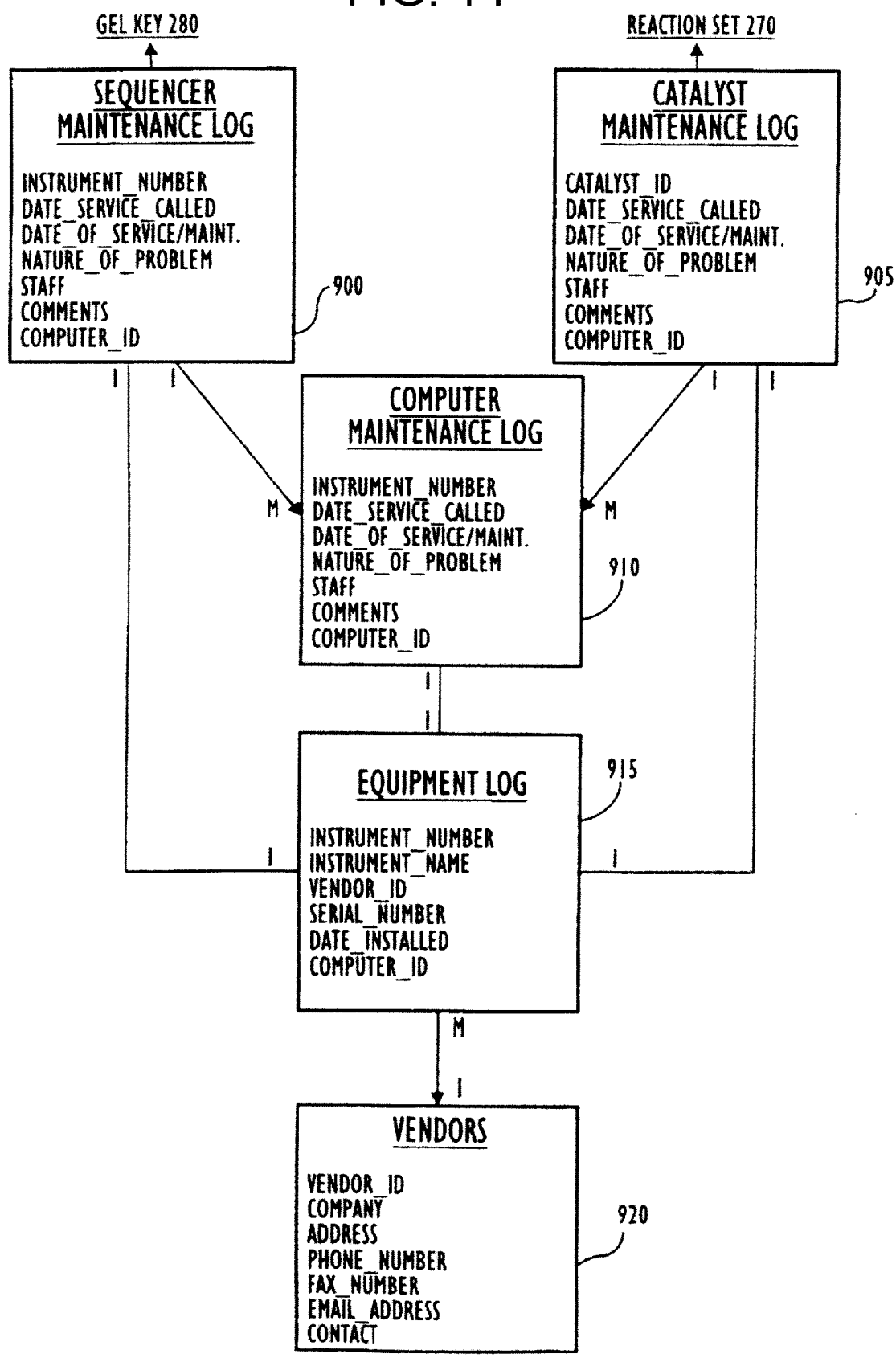
Figure 15:
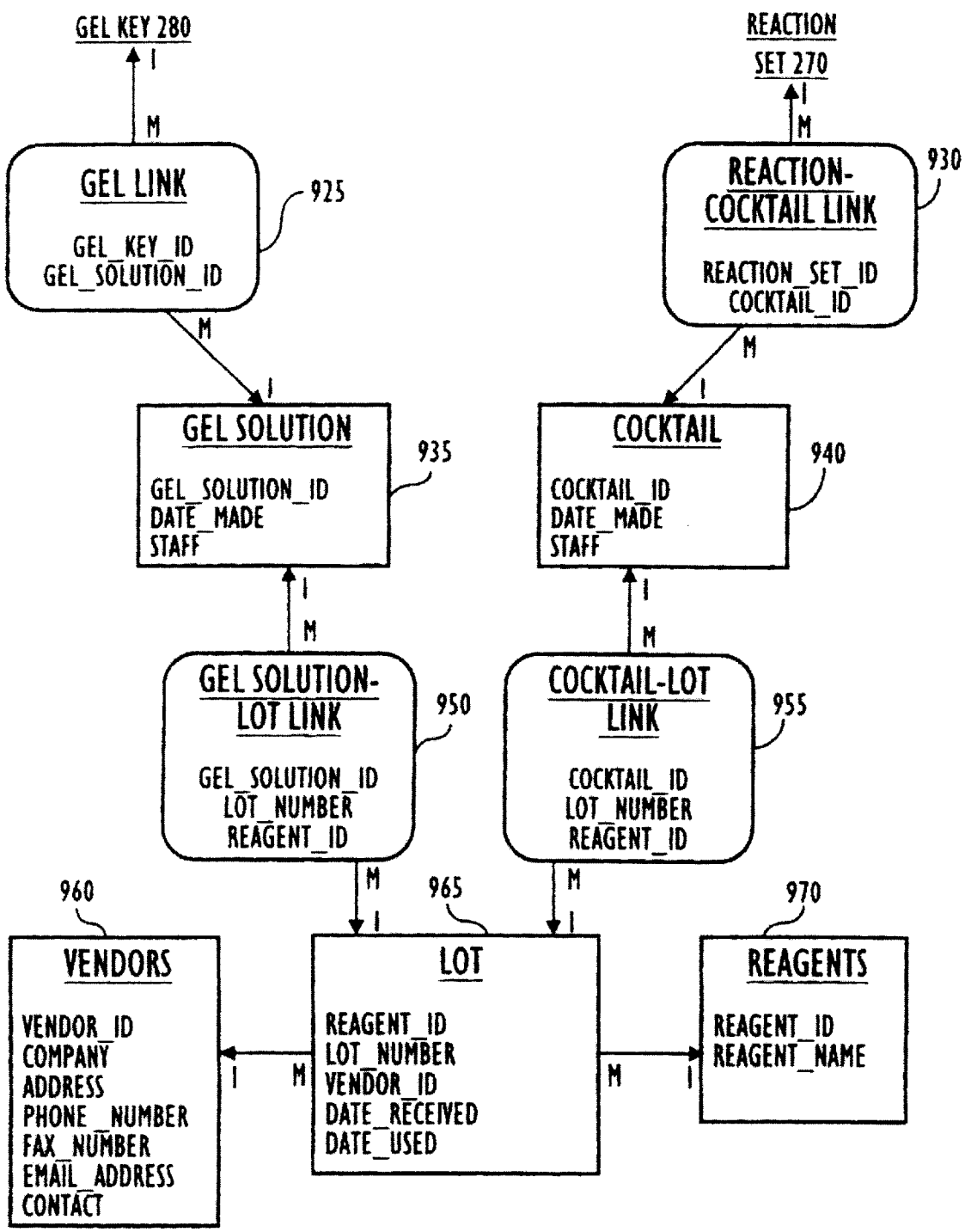

The data related to the process of sequencing the cDNAs is stored in the sequencing category of the database (FIG. 13). This category stores information relating to specifications for each sequencing gel: the conditions under which it was run, the time required for the gel run, the individual machine or instrument used, staff involved in the sequencing procedure, and biological preparation of the source tissue are recorded. Since a single clone may be sequenced multiple times, information connecting the clone with each sequencing procedure performed is recorded. This category includes a sequencing log table 300, a reaction set table 270, a sequence archive table 290, and a gel key table 280. The specification of the sequence and related information are stored as attributes in the sequencing log table 300. Information regarding the individual experiments in the sequencing reactions are stored in the reaction set table 270. The sequence archive table 290 stores information on the history of different sequencing attempts of clones. A clone sequencing link table 260 links the clone log table 250 of FIG. 12 with the sequencing log table 300. The sequencing link table 260 contains a clone_ID attribute, which is identical to the clone_ID attribute in the clone log table 250, and a sequencing _log_ID attribute, which is common with the attribute in the sequencing log table. The tracking of gel information is reflected by a gel key. The data stored in the gel key table 280 include the conditions under which the gel is run, the time the gel is run, the machine used, the staff used, and the status of the end product.

In a preferred embodiment, two additional categories document the sequencing process. First, the sequencing equipment category (FIG. 14) contains tables documenting the maintenance of the machines used in the sequencing process and the vendors from which products and machines used in the sequencing are purchased, e.g. sequencer maintenance log table 900, a catalyst maintenance log table 905, a computer maintenance log table 910, a general equipment log table 915, and a vendor table 920. Second, the sequencing reagents table (FIG. 15) stores information regarding sequencing reagents in tables, e.g. a gel link table 925, a reaction cocktail link table, a gel solution table 935, a cocktail table 940, a gel solution lot link table 950, a cocktail lot link table 955, a vendors table 960, a lot table 965, and a reagents table 970.

Experimental sets of sequences may be stored in the database in the express sets category (FIG. 16). This category includes an express link table 370, a clone variant table 380, an experimental set table 390, a cleanup table 390, and a re-sequencing table 410. Express link table stores sequence sets which have higher priority (e.g., are heavily used in analysis). Higher priority sequences are given unique identifiers and handled in separate experimental procedures. The clone variant table 380 refers to sequences flagged by an individual investigator as deviating for some reason from other sequences from a single clone. The variants are evaluated by that scientist, collaborator, or customer and appropriate action taken. The experimental sequences stored in the experimental set table 390 may be homologous to known sequences, allelic to known sequences, or mutant variants which have been flagged but not yet categorized. The cleanup table 400 stores data reflecting the addition of extra steps to the protocol. These additional steps must at times be added to the basic sequencing methods in order to improve readability of sequences. The re-sequencing table 410 tracks repeated sequencing procedures done to confirm a sequence or to gain more data from a sequence. The express sets category is related to the clone preparation category by the common attribute Clone_ID, found in the clone log table 250 and the express link table 370.

Access to the Curated Database

The curated database preferably has a user-friendly interface, which is preferably created in HTML for access with Web browsers known in the art, e.g. Netscape.

Exemplary Full-length Sequences Stored in the Database

The sequences stored within the database provide information on the expression profiles of potential test sequences. One important application of this is the ability to relate the frequency of expression of all or any of these sequences in a test individual with the frequency of expression in a control group of individuals to determine differences. A determination of differences of particular sequences allows comparison analysis of normal samples with diseased or potentially diseased sample. Information of this nature is extremely powerful, as it can be utilized in clinical diagnostics, prognostics, patient treatment, etc.

An exemplary group of sequences found within the present invention are sequences that display differential expression in diseased and non-diseased tissue, and specifically sequences that have differential expression profiles in normal and cancerous tissues. SEQ ID NOS: 1 and 2 are polynucleotide sequences PANC1A and PANC1B, which are associated with pancreatic cancer. SEQ ID NO:3 encodes a novel homolog of the known gene bcl-2, which is known to regulate apoptosis. Since apoptosis specifically targets and kills defective cells, a disruption in the expression of the genes involved in apoptosis is often part of the oncogenesis process. SEQ ID NOS: 4 and 5 encode steroid binding proteins that are differentially expressed in breast cancer. SEQ ID NO:6 encodes a novel human tumor suppressor protein, human Doc-1. Doc-1 is a cellular gene that is structurally altered during oral carcinogenesis, and is expressed in normal, but not in transformed oral keratinocytes. SEQ ID NO:7 encodes a novel prostate-specific kallikrein, HPSK, that is characterized as having chemical and structural similarity to PSA. SEQ ID NO:8 encodes a human tumor suppressor gene predicted to interact with stathmin, a cytosolic phosphoprotein that functions in cell growth and differentiation. SEQ ID NO:9 encodes TUPRO-2, a tumor suppressor gene characterized as having similarity to Doc-1. Finally, SEQ ID NO: 10 encodes a human mammoglobin homolog, a mammary-specific steroid binding protein of the uteroglobin gene family. Disregulation of gene expression of molecules such as mammoglobin is known to result in disease development or progression and have been linked to neoplastic disorders.

The presence of such sequences in the database, combined with the powerful search capabilities and access to the annotated information, allows the invention to be a highly useful tool for both research and clinical purposes. The expression patterns of such sequences in different tissues, and the ratio of this expression with other sequences contained in both the internal and external databases, is valuable for the determination and treatment of human disease. It has applications in modeling of molecular interactions by correlating potential interacting molecules based on expression dependencies. Numerous other applications would also be apparent to one skilled in the art.

Use of the Internal Database

The structure and methods of data entry of the database allow many different types of analysis to be performed, both within the internal database and between sequences in the internal database and sequences in publicly available databases. The automated bioanalysis of the sequences enhances this analysis by masking or removing sequence elements that may hinder meaningful comparisons. The organization of the database facilitates analysis by providing mechanisms by which queries may be done quickly and efficiently, both within the internal database and with other external databases. The relational nature of the internal database thus provides a more comprehensive analysis, without the need to reformulate each search for each separate database.

Query Sequence Comparison cDNA sequence comparisons can involve a combination of comparing sequences within a clustered data set, comparing sequences within the internal database, or comparing sequences with those in external databases. Reference sequences in the internal database representing the frequency with which an RNA transcript appears in a sample may match with several different clones containing all or part of the same gene.

Figure 17:
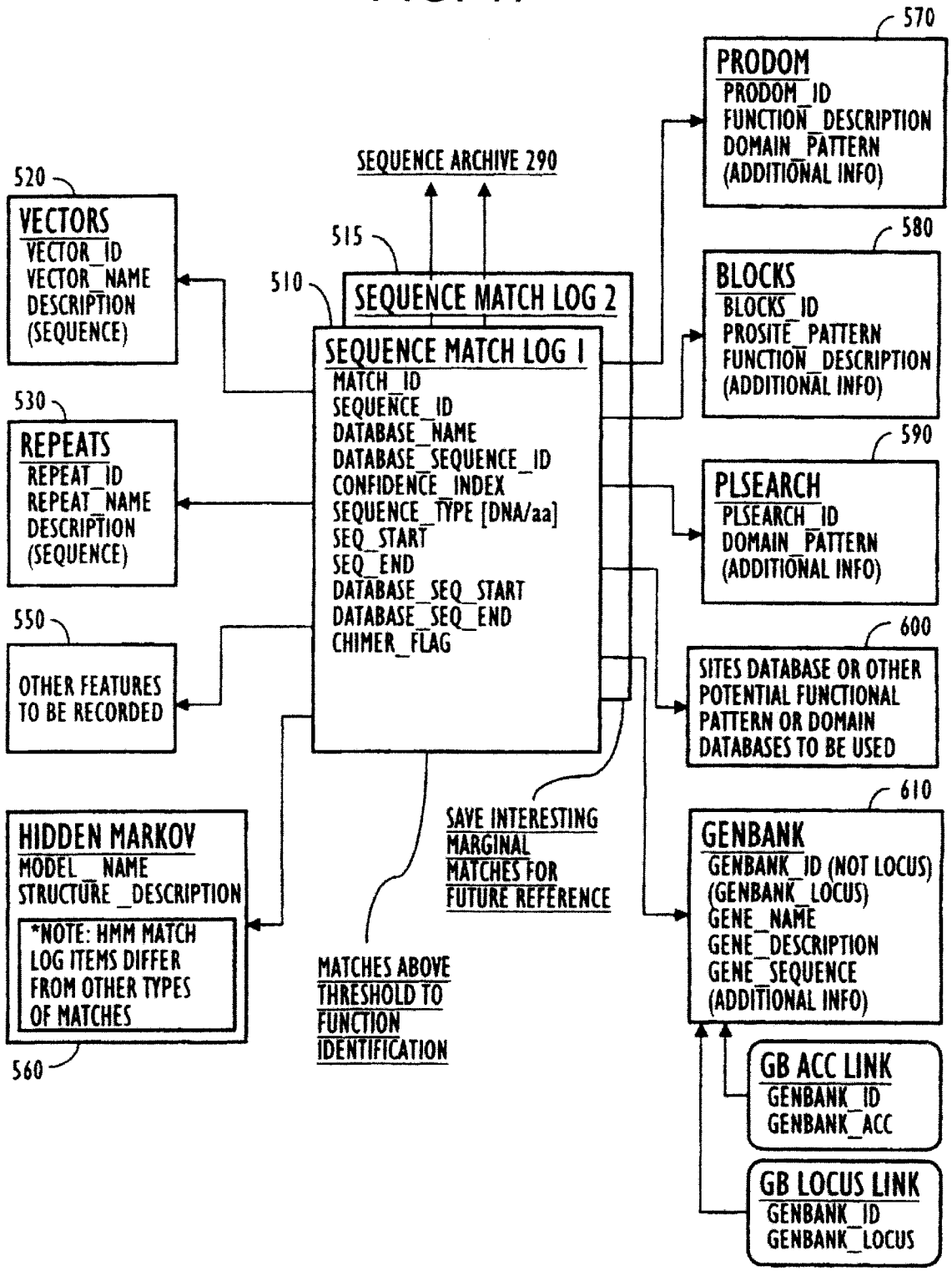
FIG. 17 illustrates an example of the sequence and comparison data as stored in the relational database.

Data relating to sequence comparison is organized and stored in the sequence comparison portion of the database (FIG. 17). This storage area includes tables containing information about the quality of the sequence matches in sequence match logs, as well as tables containing information about other features of compared sequences. The sequence comparison portion also contains information found during accession of external databases (e.g. Genbank 610, ProDom 570, Blocks 580, PL search 590 and other databases 600). These databases may provide information on homology, functional motifs or domains, and protein patterns of the compared sequences that may be predictive of activity.

A sequence comparison that results in a match is stored in sequence match log tables 510 and 515. Both tables have identical attributes, but differ in the predetermined product scores necessary for matches. Additional information contained in both the first and second sequence match log tables includes location information, i.e. the database from which the matched sequence originates, and scores indicating the percent identity of the match. Quality match scores may also be stored in a separate record, since the scoring methods may vary depending upon the algorithms used in different databases that may contain matched sequence. The sequence match logs table 510 is linked to the sequence archive 290 by the common attribute sequence_ID. The sequence match logs 510 and 515 are also linked to tables containing information regarding a matched sequence's vector name and description (vector table 520), motif or repeat sequences (repeat table 530), and other notable features as determined by automated bioanalysis (other features to be recorded table 550).

Function Identification

Figure 18:
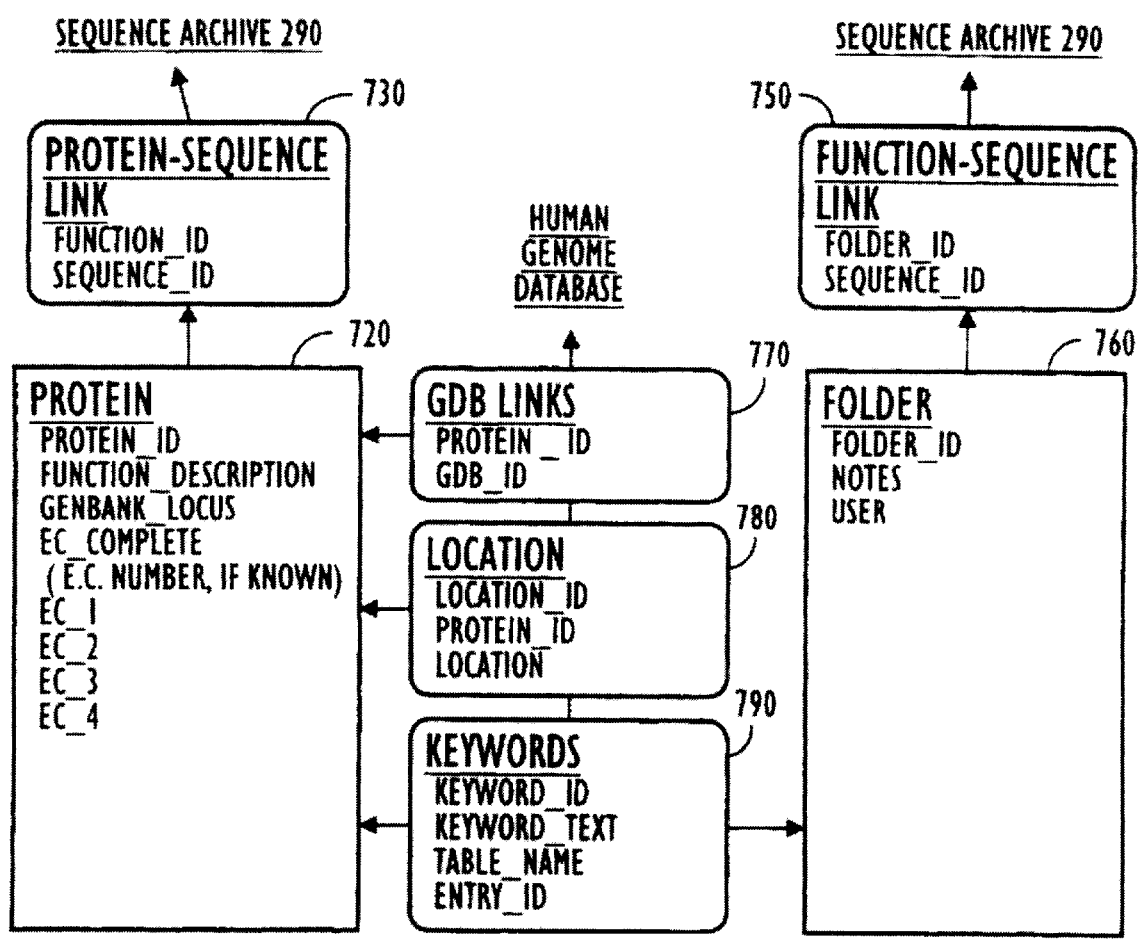
FIG. 18 illustrates the determination and storage of function identification of the predicted gene product of the cDNA sequences in the relational database.

Matched sequences may then be subjected to function identification to better determine the potential function of the predicted gene products. Data related to function identification is stored in tables in the function identification category (FIG. 18). Tables in the function identification category can include a protein table 720, a protein-sequence link table 730 (which links the protein identity to the sequence archive), a folder table for notes 760 and a location table 780 (which provides information on the known or predicted cellular location of the protein. Identification of a predicted protein structure and/or function may be determined using any of the available function or domain databases.

The Genbank location or locus and the international EC number (enzyme or protein classification) are also stored in the protein table 720. Each entry in this table corresponds to one or more sequences from the sequence archive table 290 which is conclusively identified with respect to its function. Protein table 720 has the attribute protein_ID in common with the protein-sequence link table 730. The sequence archive table 290 has the attribute sequence_ID in common with the protein-sequence link table 730.

Each entry in the folder table 760 contains unstructured annotations for one or more sequences from the sequence archive table 290 which had interesting but inconclusive matches with other databases. Any type of annotation, footnote, or remark can be recorded in the Folder table 760. This permits a user to store desired information without complicating other records in the database with information from inconclusive matches.

A user may search the internal database using keywords and a specification of tables to search with that key word. Thus, for example, a user could search the database for all sequences predicted to function in a particular tissue or cell type. Alternatively, keywords for a specific protein function, such as "tyrosine kinase," can be used to identify sequences encoding proteins predicted to have this function. Queries can be stored in the keywords table 790, with each query given a unique keyword_ID. Using the keyword_ID, a user can access all files that pertain to the query. The function-sequence link table 750 connects predicted protein function to the sequence archive table 290 through the common attribute sequence_ID.

A location table 780 stores information concerning the physical location of a sequence within the cell. The location table is linked to the protein table 720 by the common attribute protein_ID. In a preferred embodiment of the invention, this attribute consists of the categories cytoplasmic (cytoskeleton), cytoplasmic—intracellular membranes, cytoplasmic—mitochondria, cell surface, and secreted.

The genome database table 770 links the relational database to the Human Genome Database. The genome database links table has the attribute protein_ID in common with the Protein table 720 and links to the Human Genome Database via attribute GDB_ID.

Gene Information Analysis

Gene information analysis is an assessment of the annotation information related to a particular sample or library. Information on sequences of interest may be further investigated by accessing the sequence information of the project, and if desired the sequence of the representative clone for the master cluster. This analysis allows a user to access a project, determine the sequence or sequences of interest, and access annotation information relating to other clones in the cluster or project, etc.

Transcript Imaging

A transcript image is a computer image that displays each of the transcripts expressed with a certain sample or library, including multiple copies of a single transcript. Transcript imaging provides information on the relative abundance of an expressed genes in one or more libraries. This analysis is based on both the cluster and GenBank match information. The libraries used in the query are displayed in alphabetical order by tissue category. The transcript imaging results screen shows the representative clone for each clustered group of clones, along with cluster, abundance, and match information. Each group corresponds to one line of the transcript image. This information collectively is the transcript image for the particular library.

Abundance information can provide useful information on the quantity of expression of a sequence. Since specific disease states can be associated with increased expression of a gene in a sample, such information can be useful as "markers" in diagnosis and prognosis. Moreover, expression of certain genes has been correlated with either positive or poor prognosis of specific diseases. Expression of other genes may be indicative of a cell or tissue type, and may be useful in determining the cell type of origin for tissues in an unknown sample. The abundance of expression of a gene in libraries derived from normal tissues can define a standard for normal (e.g. non-disease affected) tissue. Abundance analysis can also provide information to identify evolutionary differences by determining levels of gene expression of related genes in libraries from different species.

Electronic Northerns

An electronic Northern has two objectives: to determine the libraries in which a given gene is expressed, and to determine abundance levels of gene expression in the libraries in which it is expressed. An analysis of the levels of transcript expression is performed using the transcript image of each library or sample examined. The abundance of the expression is then shown for each selected sample. In the internal database, an electronic Northern will display library names, library description, and abundance information for the selected clones. The associated hypertext links can direct the user to other areas of the database for more detailed library and clone information.

The electronic Northerns mimic conventional "wet lab" Northerns done in a laboratory in that they allow users to compare relative levels of the expression of a single gene or gene family. Electronic Northerns can be performed for different tissue types of a single patient, for the same tissue type from different patients (e.g. to develop a standard for normal expression), for the same tissue type of a single species at different stages of development (i.e. an electronic developmental Northern), for the same tissue type across species (e.g. evolutionary studies), and for normal and abnormal samples derived from the same tissue type (e.g. normal tissue versus cancerous tissue). Thus, electronic Northern analysis can provide important information on expression for a variety of uses. Expression may give insight on the timing of expression, potential function of the gene product, and involvement in the disease state.

Electronic Commonality Analysis

Electronic commonality analysis identifies the clones contained in both a target library and in a selected background library. Transcript images are produced for each of the libraries, and the information run through a programmed computer to compare the expression of each gene. The results differ from producing a transcript image because normalized abundances are used to determine a ratio of expression between the two libraries. Genes most highly expressed in the target library are found at the top of the list, whereas those at the bottom represent genes preferentially expressed in the background library. Pooled commonality analysis identities master clusters containing clones in at least one of the target set libraries and at least one of the background set libraries above the chosen background abundance stringency.

Electronic commonality information is determined through a significance value calculation, which displays each of the sequences expressed in either the query or the background library. The calculation is based on abundance differences between sequences represented in the two libraries, and is reported as a Sig value. The top listing result is the master cluster with the most statistically relevant difference in abundance between the two libraries. This master cluster will have the lowest Sig value, indicating that the clone abundances are less likely to be due to random chance. The threshold for commonality analysis is determined by designating a Sig value at which the abundance comparisons are below a determined abundance stringency.

Commonality analysis is preferable for direct comparison of commonly expressed sequences in two or more libraries. Commonality analysis differs from other types of analysis, such as transcript imaging, in that it excludes sequences expressed in one but not the other libraries examined in the query. Commonality analysis is particularly useful in determining similarities between a query library and a selected library in the database.

Subtraction Analysis

An electronic subtraction analysis "subtracts" the clones in a background library from those in a library of interest in order to identify differential clones, i.e. clones that are present only in either one or the other of the libraries examined. Transcript images are produced for each of the libraries, and this information analyzed to determine the relative gene expression in each library. Subtraction analysis differs from transcript image analysis because only a subset of the sequences in a chosen target library are displayed. Pooled subtraction analysis will display only the master clusters that have clones in at least one library from a query set (equal to or above a selected target abundance threshold) but not in any of the background set libraries above the chosen background abundance threshold.

Electronic subtraction analysis is also determined through a significance value calculation, which determines each of the sequences expressed in either the query or the background library. The calculation is based on abundance differences between sequences represented in the two libraries, and is reported as a Sig value. The Sig value is used to identify sequences present at a determined level in one library, but not in the comparison library. The threshold for subtraction analysis is determined by designating a Sig value at which the abundance comparisons are above a determined abundance stringency. The stringency may be a complete absence of expression in one of the two sets.

Subtraction analysis can be used in a number of applications. For example, subtraction analysis can be used to identify genes whose expression is specific to a given cell type. Subtraction analysis may also assess gene expression in tissues from different developmental stages or stages in disease progression, thus identifying genes involved in differentiation or de-differentiation. Such information can be used subsequently to aid in the identification of the tissue of a sample of unknown derivation.

Subtraction analysis can also identify novel genes specific to a selected cell type. For example, subtraction analysis between a library of cardiac tissue and skeletal muscle tissue will discard many of the genes involved in general muscle maintenance, and reveal the genes specific to each tissue, thus facilitating identification of genes expressed solely in either the cardiac tissue or the skeletal muscle tissue. Moreover, genes identified via subtraction analysis are more likely to have a function of specific importance to the organ in which it is expressed.

Protein Function Analysis

Protein function analysis allows a user to search for classes of molecules based on their functional classification. The cDNA sequences of the database can translated into the predicted protein sequence, and these protein sequences are used in function analysis queries. This is especially useful in a database primarily composed of full-length sequences, as the vast majority of cDNAs contain the entire coding region for the protein.

Protein function analysis preferably involves consists numerous divisions of analysis. First, analysis is performed with an enzyme hierarchy consisting of enzymes assigned in exact accordance with the Enzyme Commission (EC) list, thereby comparing the predicted protein sequence of the query sequence to enzyme structures with known functions. Preferably, the results are displayed with Internet links to the Enzyme Nomenclature Database at the Swiss-Prot site maintained by the University of Geneva. Second, the molecular hierarchy analysis divides proteins into functional categories using a structure and nomenclature similar to that of the EC list. Finally, the biological hierarchy analysis divides proteins based on their level of functioning, i.e. cellular-, tissue-, or organism-level.

Protein function analysis can elucidate the predicted activity of a novel gene product by identifying motifs with specific functions. This function may be enzymatic (e.g. a phosphatase domain), structural (e.g. a helix-loop-helix, indicating DNA binding activity), locational (e.g. a transmembrane region, indicating that the protein is located in a membrane), etc. Identifying potential functions for novel genes is a powerful way to determine the role such a gene product may play in the sample of origin. Differences in the sequence of such domains in different samples can provide information on the conservation of amino acids in the domains, which can identify the critical residues for the functioning of a domain of this sort. Such residue substitutions also may change the function of the domain, and comparison may identify proteins with either decreased or enhance function in the domain.

Accessing Annotated Information

Once a search has been performed in the database of the invention, information regarding match samples or libraries can be accessed through the relational database organization. If a query sequence matches to a reference sequence, a user can track and manipulate the annotated information on the reference sequence using one or more relational databases, e.g., via an integrated Ethernet network. The computerized storage and retrieval system can be searched to determine source tissue and source organ information. Patient medical history (such as age, gender, and treatment status) and pathology information of the sample can also be retrieved. Pathology information on the sample can be retrieved. With this information, specific match sequences can be chosen based on similarities or differences in the samples used to generate the cDNA sequences.

EXAMPLES

The following examples are put forth so as to provide those of ordinary skill in the art with a complete disclosure and description of how to make and use various constructs and perform the various methods of the present invention and are not intended to limit the scope of what the inventors regard as their invention. Efforts have been made to ensure accuracy with respect to numbers used (e.g. amounts, concentrations, particular components, etc.) but some deviations should be accounted for.

Example 1

Use of the Database for Gene Discovery

A new class of ATP receptor molecules was described in Nature 377:432. Subsequent to this discovery, the database programming system of the present invention was used to identify a novel member of this family, $P2X_3$.

First, the nucleotide sequence encoding the $P2X_3$ receptor was retrieved using the database Sequence Retrieval Query using its GI number. This nucleotide sequence was pasted into the databases BLAST search screen for screening against all sequences contained within the database. The program tblastn was chosen as the search program. This performed a protein search against the translated sequence information within the internal database of the invention. Several sequences matched the query with good Product scores.

Examination of the alignment of the $P2X_3$ sequence with the matched sequences showed that these sequences were the similar to, but not identical to, the query $P2X_3$ sequence. These clones constituted a set of potentially novel members of this family of receptors. Others could be members of already-identified genes. Clones were determined to be novel homologues or new cDNA sequences if: 1) they matched a sequence from any database other than GenBank Primates; 2) they are listed as unique within the internal database; or 3) they have a Product score below 40. The annotation in the database was used to make this determination, since exact matches were previously annotated and therefore readily detected.

Example 2

Use of the Database for Diagnosis of Infectious Disease

The clinical diagnosis of a bacterial or fungal infection may be particularly difficult in certain patients, such as young infants, children, and immunocompromised individuals using conventional techniques. Clinical algorithms have been developed for the diagnosis of bacteremia and other infections in young children, but the discriminatory ability of these algorithms remains controversial. Polymerase chain reaction (PCR) amplification of bacterial and fungal DNA is rapid and sensitive, but many of the methods presently in use are often too specific for the initial diagnosis.

The database of the present invention provides a fast and accurate method for screening an immunosuppressed patient for a vast array of infectious organisms. A rapid and reliable method for identification of bacteria or fungi in blood and other bodily fluids would reduce hospitalization and medical costs, as well as affording better patient care. Quick and accurate diagnosis will also reduce exposure of immunosuppressed patients to infections associated with hospital admission, and decrease morbidity and mortality among those managed as outpatients.

A peripheral blood, cerebrospinal fluid, synovial fluid or other aspirated tissue fluid is taken from a patient suspected of having an infectious disorder. Sequences obtained from this sample corresponding to the resulting cDNA library are entered into the database as a query. The query is run against uninfected tissue of the same category, and the libraries compared. This comparison is can be done using electronic commonality analysis, to examine whether the sample's sequences are similar to uninfected sequences, or using subtraction analysis, to determine the presence of foreign microorganismal sequences in the sample library. The presence of foreign sequences in the sample library is indicative of infection in the patient from whom the sample was taken.

Example 3

Use of the Database to Confirm Diagnosis of Infectious Disease

The presentation of different diseases and disorders may make diagnosis difficult. In pathogenic diseases, catching the disease in an early state may allow the prevention of irreversible physiological damage. The database of the present invention can confirm the gene expression of a specific organism, allowing the identification of a disease in a crucial early time period. This is especially helpful in differentiating between diseases with similar presentations.

One such infectious disease, Lyme disease, is particularly difficult disease to diagnose because initially it presents with flu-like symptoms, has an extended latency period, and its presentation after the incubation period are very similar to other neurological and immunological disorders, such as rheumatoid arthritis, Bell's palsy, and multiple sclerosis. Diagnosis is thus difficult both in the critical early stage of the disease, when it is still treatable and neurological damage is preventable, and in the later stages of the disease, when differential diagnosis is required. Lyme disease can be effectively and permanently treated with sufficient doses of antibiotics during the early stage.

The bacterium *B. burgdorferi* is the pathogen responsible for Lyme disease. Diagnosis is possible by visualization of whole *B. burgdorferi* by culturing a specimen from an affected person. This process, however, is slow and poor yields are generally obtained. Other methods are available, such as immunoassays and the Polymerase Chain Reaction (PCR) to detect *B. burgdorferi* DNA in a patient's sample. These tests are difficult, however, because levels of *B. burgdorferi* protein in samples are low, and PCR is affected by contamination of related organisms and the consequential false positive results.

The database can be used to diagnose Lyme disease in a more methodical and reliable manner. Since *B. burgdorferi* is notoriously difficult to culture, an alternate approach can be taken. A peripheral blood, cerebrospinal fluid, synovial fluid or other aspirated tissue fluid is taken from a patient suspected of having Lyme disease. Sequences obtained from this sample corresponding to the resulting cDNA library are entered into the database as a query. Since the level of *B. burgdorferi* transcripts within the patient sample are likely to be low, the cDNA library from the sample can be normalized prior to sequence analysis and query to increase the likelihood that *B. burgdorferi* transcripts will be detected. The query is run against normal tissue of the same category without *B. burgdorferi* transcripts, and the libraries compared. This comparison is preferably an electronic commonality analysis, to examine whether the sample sequences are similar to the *B. burgdorferi* sequences. Subtraction analysis can also be used to determine the presence of *B. burgdorferi* sequences in the sample library. The presence of *B. burgdorferi* sequences in the sample library is indicative of Lyme disease infection in the patient from whom the sample was taken.

cDNA libraries will also be made from patients affirmatively diagnosed with Lyme disease. These sequences may be used in library comparisons with potentially affected individual's samples to aid in diagnosis. This category of gene sequences can also potentially identify a human gene sequence that is elevated or suppressed in response to *B. burgdorferi* infection. To confirm a diagnosis, or to better determine a diagnosis, the sequences may also be compared to external databases. In lieu of culturing the *B. burgdorferi* for sequence data, known data in existing databases corresponding to transcript information of *B. burgdorferi* can be accessed in other, related organismal databases. This external information can confirm the diagnosis.

Example 4

Use of the Database for Identification of Malignant Tissue

Development of breast cancer is associated with multiple genetic changes associated with alterations in expression of specific genes. Breast cancer tissues express genes that are not expressed, or expressed at lower levels, by normal breast tissue. Thus, it is possible to differentiate between non-cancerous breast tissue and malignant breast tissue by analyzing differential gene expression between tissues. In addition, there may be several possible alterations that lead to the various possible types of breast cancer. Thus, different types of breast tumors (e.g., invasive vs. non-invasive, ductal vs. axillary lymph node) can be differentiable one from another by the identification of the differences in genes expressed by different types of breast tumor tissues (Porter-Jordan et al. 1994 Hematol Oncol Clin North Am 8:73–100). Breast cancer can thus be generally diagnosed by detection of expression of a gene or genes associated with breast tumor tissue. Where enough information is available about the differential gene expression between various types of breast tumor tissues, the specific type of breast tumor can also be diagnosed.

The expression of the two steroid binding proteins encoded by SEQ ID NOS: 4 and 5, collectively termed hSBPs, can be used in the diagnosis and management of breast cancer. The differential expression of hSBPs in human breast tumor tissue, as disclosed in U.S. patent application Ser. No. 08/747,547, can be used as a diagnostic marker for human breast cancer. Detection of breast cancer can be determined using expression levels of hSBP itself. In addition, development of breast cancer can be detected by examining the ratio of hSBP to the levels of steroid hormones (e.g., testosterone or estrogen) or to other hormones (e.g., growth hormone, insulin). Thus expression of hSBP1 and/or hSBP2 can also be used to discriminate between normal and cancerous breast tissue, and to discriminate between different types of breast cancer.

The database is a useful tool in determining the diagnosis of breast cancer. Diagnosis of breast cancer involves a comparison of expression levels of hSBPs, and ratio of this expression with the expression of other hormones, in non-malignant breast tissue samples in comparison to non-diseased tissue. First, a sample of the potentially malignant tissue is surgically removed from a patient. Then a cDNA library is constructed from the mRNA extracted from the sample. Once the sequence data is obtained for the cDNA library corresponding to this particular sample, this information is entered into the database. From here, a transcript image is created from the sequence data to determine the relative abundance of all transcripts within the peripheral blood sample. This procedure gives an overall molecular profile of the peripheral blood sample. Library comparison is carried out between: 1) a background, normal breast tissue library from a normal control in the female reproductive tissue category and 2) the library of the potentially affected individual. A transcript image comparison between the samples provides information on relative levels of hSBP as well as the ratio of hSBP to other hormones in the tissue of interest compared to normal. Moreover the "normal" tissue comparison selects sequences that correspond to a patient that is very similar to the query individual in race, age, clinical history, etc in order to limit other biological factors.

Example 5

Use of the Database for Prognostic Purposes

The expression of certain genes has been correlated to prognosis of a disease state. For example, prostate-specific antigen (PSA) present in the peripheral blood has been shown to have prognostic significance in relation to survival of patients with metastatic androgen-independent prostatic carcinoma (AIPC). Measurement of the expression of HPSK (encoded by SEQ ID NO:7) is also of prognostic value in AIPC, as this molecule is prostate-specific and is predicted to serve a biological function similar to PSA. The levels of HPSK in patients with prostate cancer as compared to normal individuals can be predicative of the extent and nature of the cancer. Moreover, determining levels of transcript of prognostic indicators such as HPSK in peripheral blood, as opposed to a single serum measurement, is a superior predictor of survival. (Ghossein et. Al. (1997) *Urology* 50:100–105).

The database is useful in determining the prognosis of patients, such as those with AIPC. First, a peripheral blood sample is taken from a patient. Then a cDNA library is constructed from the mRNA contained within this peripheral blood sample. Once the sequence data is obtained for the cDNA library corresponding to this particular sample, this information is entered into the database. From here, a transcript image is created from the sequence data to determine the relative abundance of all transcripts within the peripheral blood sample. This procedure gives an overall molecular profile of the peripheral blood sample. This is important not only for a present determination of the gene transcripts present in the sample, but also for longer-term monitoring of the same patient. If samples are taken from the same individual over a period of time, differences that are specific to that patient may be identified. The organization of the database allows the quick and accurate direct comparison of transcript analysis over time through the storage of the sequence information and the production of transcript images from such information for later comparison.

Second, library comparison is carried out between: 1) a background, normal peripheral blood library from a normal control in the male reproductive tissue category and 2) libraries from peripheral blood samples of one or more affected individuals. The comparison between libraries may be a significance value correlation, an electronic commonality correlation, a subtraction analysis, or a comparison of transcript images between samples. In a preferred method, a gene transcript image is created from the sample sequence information, and the levels of HPSK transcript measured in relation to the other transcripts in the sample. This can be compared to other gene transcript images from the male reproductive tissue library that correspond to a normal control and to other samples from patients with known poor prognosis. Characteristics such as age, ethnicity, additional health problems, etc. may be similarly matched in the library comparison. The comparison can be used to determine the present prognosis of the patient.

Example 6

Use of the Database to Determine Treatment Options

Recent advances in the pathogenesis of certain cancers has been helpful in determining patient treatment. The correlation of novel surrogate tumor specific features with response to treatment and outcome in patients has defined certain prognostic indicators that allow the design of tailored therapy based on the molecular profile of the tumor. These therapies include antibody targeting and gene therapy.

Once a patient is diagnosed with an ovarian tumor, the tumor is removed by a surgical procedure. A portion of the tumor then becomes a sample for cDNA library construction. Once the sequence data is obtained for the cDNA library corresponding to this particular sample, this information is entered into the database. From here, two procedures can be carried out. First, a transcript image is carried out to determine the relative abundance of transcripts within the sample of the ovarian cancer. This first procedure gives an overall molecular profile of the ovarian tumor Second, library comparison is carried out between: 1) a background, normal ovarian tissue cDNA libraries, contained within the female reproductive tissue category of the database, and the cDNA library corresponding to the sample, and 2) between benign ovarian hyperplasia cDNA libraries, also contained within the female reproductive tissue category of the database, and the cDNA library corresponding to the sample. The comparison between libraries may be a significance value correlation, an electronic commonality correlation, a subtraction analysis, or a comparison of transcript images between sample tissue types. This second procedure allows a molecular comparison between the expression found within the sample compared with both normal tissue and with a benign growth of that tissue.

The roles of certain proteins, in particular tyrosine kinase receptors such as c-erbB2 and c-fms, in the pathogenesis of ovarian cancer has been correlated with disease progression. (Katso et.al. (1997) *Cancer Metastasis Rev* 16:81–107). The delineation of these roles in the pathogenesis of ovarian cancer has lead to the development of new approaches to oncological therapy, such as anti-c-erbB2 monoclonal antibody therapy. The ability to determine the molecular nature of a particular sample and a comparison in the database will allow a tailored treatment based on its molecular profile. For example, the anti-c-erbB2 monoclonal antibody therapy may be appropriate in a sample which shows elevated levels of the c-erbB2 transcript, whereas it may not be in a sample which does not show such elevation.

In addition, the level of expression of certain genes may be indicative of a poorer prognosis, and may therefore warrant more aggressive chemo- or radio-therapy for a patient that may otherwise be provided. Alternatively, a promising transcript image may provide impetus for not aggressively treating a particular patient, thus sparing her the deleterious side effects of aggressive therapy. Thus, using the database of the invention to determine the transcript image and use of the molecular profile in library comparison allows a determination of the best possible treatment for a patient, both in terms of specificity of treatment and in terms of comfort level of the patient.

The foregoing invention has been described in some detail by way of illustration and example for purposes of clarity of understanding. It is readily apparent to those of ordinary skill in the art in light of the teachings of this invention that certain changes and modifications may be made thereto without departing from the spirit or scope of the appended claims.

Although the invention has been described with reference to the presently preferred embodiments, it should be understood that various modifications can be made without departing from the spirit of the invention. Accordingly, the invention is limited only by the following claims.

What is claimed is:

1. A computerized storage and retrieval system of biological information, comprising:

a data entry means;

a display means;

a programmable central processing unit; and a data storage means having cDNA sequences and annotated information on attributes of a cDNA sequence electronically stored in a relational database;

wherein the stored sequences are annotated and organized in a curated clustering arrangement, and wherein the annotated information for a cDNA sequence can be directly accessed through the relational database.

2. The computerized storage and retrieval system of claim 1, wherein the central processing unit is programmed with the ability to perform gene annotation analysis, generate transcript images, perform transcript image analysis, perform subtractive analysis, perform electronic Northern analysis, or perform electronic commonality analysis.

3. The computerized storage and retrieval system of claim 1, wherein the central processing unit is programmed to perform automated bioanalysis on the stored cDNA sequences.

4. The computerized storage and retrieval system of claim 3, wherein the automated bioanalysis comprises:

editing a plurality of sequences; and annotating and organizing said sequences.

5. The computerized storage and retrieval system of claim 4, wherein the sequence editing comprises the steps of:

identifying and removing vector sequences;

identifying and removing non-informative search motifs;

identifying and removing cloning and sequencing artifacts; and identifying and masking low information sequences.

6. The computerized storage and retrieval system of claim 4, wherein the automated bioanalysis further comprises the steps of:

transcript extension; and transcript expansion.

7. The computerized storage and retrieval system of claim 1, wherein the stored cDNA sequences are comprised of SEQ ID NOS. 1–10.

8. The computerized storage and retrival system of claim 1, wherein the information pertaining to the cDNA sequences is stored in a plurality of tables.

9. The computerized storage and retrieval system of claim 8, wherein the tables comprise the attributes of library preparation, clone preparation, sequencing, sequencing equipment, sequencing reagents, function identification, and express sets.

10. The computerized storage and retrieval system of claim 1, wherein the storage means can be searched to determine source tissue information, to determine source organ information, to determine source pathology information, or to determine source patient information.

11. A method for quantifying the relative abundance of mRNA species in a sample, said method comprising the steps of:

generating cDNA sequences from a population of transcripts found within a sample;

organizing the cDNA sequences into a curated clustering arrangement;

accessing a computerized storage and retrieval system of biological information containing reference cDNA sequence data annotated and stored in a curated clustering arrangement;

processing the sample sequence data and the reference sequence data in a programmed computer to generate an identified sequence value for each of the transcripts, said sequence value being indicative of a sequence annotation and a degree of match between a transcript from the sample sequence data and at least one transcript from the reference sequence data; and processing each identified sequence value to generate final data values indicative of a number of times each identified sample sequence value is present within the curated reference sequences.

12. The method of claim 11, wherein the sequence data is comprised of SEQ ID NOS. 1–10.

13. A method for transcript image analysis comparing two or more samples, comprising the steps of:

producing a first transcript image from the cDNA sequences of a first sample;

producing a second transcript image from the cDNA sequences of a second sample; and determining the ratio of the frequency that a cDNA sequence appears in the first and the second source samples;

wherein the ratio of the frequency that a cDNA sequence appears in the first and the second samples is indicative of the relative levels of expression of the corresponding transcripts in each sample.

14. The method of claim 13 wherein said second sample is a stored reference set of cDNA sequences.

15. The method of claim 13, wherein the first sample is from normal tissue and the second sample is from a diseased or potentially diseased sample.

16. A method for performing electronic Northern analysis comprising the steps of:

selecting libraries from samples of interest;

selecting a cDNA sequence to examine in each selected library; and determining the abundance of said cDNA sequence in each library;

wherein the abundance of cDNA sequence in each library is indicative of the location, distribution, and relative abundance of gene expression in the selected samples.

17. The method of claim 16, wherein the gene expression is determined by the abundance of a cDNA sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

18. The method of claim 16, wherein the method is used for diagnostic purposes, prognostic purposes, or determining patient treatment.

19. A method for performing electronic commonality analysis between a first sample and a second sample, said method comprising the steps of:

producing a first transcript image from the cDNA sequences of a first sample;

producing a second transcript image from the cDNA sequences of a second sample; and electronically comparing the transcript images of the sample data set and the reference data set to identify transcripts expressed in both of the two samples;

wherein said comparing identifies sequences common to both samples.

20. The method of claim 19 wherein said second sample is a stored reference set of cDNA sequences.

21. The method of claim 19, wherein the first sample is from normal tissue and the second sample is from a diseased or potentially diseased sample.

22. The method of claim 19, wherein the sample is selected from the group consisting of blood, sputum, urine, ascites fluid, cerebrospinal fluid, and biopsy tissue.

23. The method of claim 19, wherein the method is used for diagnostic purposes, prognostic purposes, or determining patient treatment.

24. A method for performing electronic subtraction analysis between a first sample and a second sample, said method comprising the steps of:

producing a first transcript image from the cDNA sequences of a first sample;

producing a second transcript image from the cDNA sequences of a second sample; and selecting a target abundance value for transcripts found in the sample sequence data and reference sequence data;

processing this information to determine the transcripts within each sequence data set that exceed the selected target abundance value; and electronically comparing the transcript images of the sample data set and the reference data set to identify transcripts expressed in only one of the two samples.

25. The method of claim 24 wherein said second sample is a stored reference set of cDNA sequences.

26. The method of claim 24, wherein the first sample is from normal tissue and the second sample is from a diseased or potentially diseased sample.

27. The method of claim 24, wherein the sample is selected from the group consisting of blood, urine, sputum, ascites fluid, cerebrospinal fluid, and biopsy tissue.

* * * * *

UNITED STATES PATENT AND TRADEMARK OFFICE
CERTIFICATE OF CORRECTION

PATENT NO.    : 6,303,297 B1
DATED         : October 16, 2001
INVENTOR(S)   : Steve E. Lincoln et al.

It is certified that error appears in the above-identified patent and that said Letters Patent is hereby corrected as shown below:

<u>Column 38,</u>
Line 64, please insert -- reference -- prior to the word "sequence".
Lines 64 and 65, Claim 12 should read as follows: The method to claim 11, wherein the reference sequence data is comprised of SEQ ID NOS. 1-10.

Signed and Sealed this

Twentieth Day of May, 2003

JAMES E. ROGAN
*Director of the United States Patent and Trademark Office*

SEQUENCE LISTING

<160> NUMBER OF SEQ ID NOS: 10

<210> SEQ ID NO 1
<211> LENGTH: 373
<212> TYPE: DNA
<213> ORGANISM: Homo sapiens
<220> FEATURE:
<221> NAME/KEY: misc_feature
<222> LOCATION: (1)...(373)
<223> OTHER INFORMATION: n = A,T,C or G

<400> SEQUENCE: 1

```
gtacggaggt gaggtttgtn accgcgattc taagaggtgg gcttttagtc cctccagacc      60
tcggctttag tgctgtctcc gcttttyttt caccttcaca gaggttcgtg tcttcctaaa     120
agaaggtttt attgggaggt aaaggtcaat gcgtaggggt agagtaagat gtcttatggt     180
gaaattraag gtaaattctt gggacctaga gaagaagtaa cgagtgagcc acgctgtaaa     240
aaattgaagt caaccacaga gtcgtatgtt tttcacaatc atagtaatgc tgattttcac     300
agnatccaag agaaaactgg aaatgattgg gtccctgtgn ncatcattga tgtcagagga     360
catagttatt tgc                                                        373
```

<210> SEQ ID NO 2
<211> LENGTH: 321
<212> TYPE: DNA
<213> ORGANISM: Homo sapiens
<220> FEATURE:
<221> NAME/KEY: misc_feature
<222> LOCATION: (1)...(321)
<223> OTHER INFORMATION: n = A,T,C or G

<400> SEQUENCE: 2

```
gtgaggtttg ttaccncgat tctgagaggt gggcttttag tccctccaga cctcggcttt      60
agtgctgtct ccgmttttct ttcaccttca cagagatgtc ttatggtgaa attgaaggta     120
aattcttggg acctagwgaa gaagtaacga gtgagccacg ctgtaaaaaa ttgaagtcaa     180
ccacagagtc gtatgttttt cacaatcata gtaatgctga ttttcacagw atccaagaga     240
aaactggaaa tgatttgggt ccctgtgacc atcattnatg tcagaggnca tagttaattt     300
gcaggaganc aaaaatcaaa a                                               321
```

<210> SEQ ID NO 3
<211> LENGTH: 528
<212> TYPE: DNA
<213> ORGANISM: Homo sapiens

<400> SEQUENCE: 3

```
atgacagact gtgaatttgg atatatttac aggctggctc aggactatct gcagtgcgtc      60
ctacagatac cacaacctgg atcaggtcca agcaaaacgt ccagagtgct acaaaatgtt     120
gcgttctcag tccaaaaaga agtggaaaag aatctgaagt catgcttgga caatgttaat     180
```

-continued

| | |
|---|---|
| gttgtgtccg tagacactgc cagaacacta ttcaaccaag tgatggaaaa ggagtttgaa | 240 |
| gacgacatca ttaactgggg aagaattgta accatatttg catttgaagg tattctcatc | 300 |
| aagaaacttc tacgcagca aattgccccg gatgtggata cctataagga gatttcatat | 360 |
| tttgttgcgg agttcataat gaataacaca ggagaatgga taaggcaaaa cggaggctgg | 420 |
| gaaaatggct ttgtaaagaa gtttgaacct aaatctggct ggatgacttt tctagaagtt | 480 |
| acaggaaaga tctgtgaaat gctatctctc ctgaagcaat actgttga | 528 |

<210> SEQ ID NO 4
<211> LENGTH: 405
<212> TYPE: DNA
<213> ORGANISM: Homo sapiens

<400> SEQUENCE: 4

| | |
|---|---|
| gtccaaatca ctcattgttt gtgaaagctg agctcacagc aaaacaagcc accatgaagc | 60 |
| tgtcggtgtg tctcctgctg gtcacgctgg ccctctgctg ctaccaggcc aatgccgagt | 120 |
| tctgcccagc tcttgtttct gagctgttag acttcttctt cattagtgaa cctctgttca | 180 |
| agttaagtct tgccaaattt gatgcccctc cggaagctgt tgcagccaag ttaggagtga | 240 |
| agagatgcac ggatcagatg tcccttcaga acgaagcct cattgcggaa gtcctggtga | 300 |
| aaatattgaa gaaatgtagt gtgtgacatg taaaaacttt catcctggtt tccactgtct | 360 |
| ttcaatgaca ccctgatctt cactgcagaa tgtaaaggtt tcaac | 405 |

<210> SEQ ID NO 5
<211> LENGTH: 495
<212> TYPE: DNA
<213> ORGANISM: Homo sapiens

<400> SEQUENCE: 5

| | |
|---|---|
| gatccttgcc acccgcgact gaacaccgac agcagcagcc tcaccatgaa gttgctgatg | 60 |
| gtcctcatgc tggcggccct ctcccagcac tgctacgcag gctctggctg cccttattg | 120 |
| gagaatgtga tttccaagac aatcaatcca caagtgtcta agactgaata caaagaactt | 180 |
| cttcaagagt tcatagacga caatgccact acaaatgcca tagatgaatt gaaggaatgt | 240 |
| tttcttaacc aaacggatga aactctgagc aatgttgagg tgtttatgca attaatatat | 300 |
| gacagcagtc tttgtgattt atttttaactt tctgcaagac ctttggctca cagaactgca | 360 |
| gggtatggtg agaaaccaac tacggattgc tgcaaaccac accttctctt tcttatgtct | 420 |
| ttttactaca aactacaaga caattgttga aacctgctat acatgtttat tttaataaat | 480 |
| tgatggcaaa aactg | 495 |

<210> SEQ ID NO 6
<211> LENGTH: 1143
<212> TYPE: DNA
<213> ORGANISM: Homo sapiens

<400> SEQUENCE: 6

| | |
|---|---|
| ggccccgccg cgcccggcgc gcccgccgcc cgggggatg tcttacaaac cgaacttggc | 60 |
| cgcgcacatg cccgccgccg ccctcaacgc cgctgggagt gtccactcgc cttccaccag | 120 |
| catggcaacg tcttcacagt accgccagct gctcagtgac tacgggccac cgtccctagg | 180 |
| ctacacccag ggaactggga cagccaggt gccccaaagc aaatacgcgg agctgctggc | 240 |
| catcattgaa gagctgggga aggagatcag acccacgtac gcagggagca agagtgccat | 300 |
| ggagaggctg aagcgcggca tcattcacgc tagaggactg gttcgggagt tcttggcaga | 360 |

```
aacggaacgg aatgccagat cctagctgcc ttgttggttt tgaaggattt ccatctttt      420 acaagatgag aagttacagt tcatctcccc tgttcagatg aaaccttgt tttcaaaatg      480 gttacagttt cgttttcct cccatggttc acttggctct gaacctacag tctcaaagat      540
tgagaaaaga ttttgcagtt aattaggatt tgcattttaa gtagttagga actgcccagg    600
ttttttttgt ttttaagca ttgatttaaa agatgcacgg aaagttatct tacagcaaac     660
tgtagtttgc ctccaagaca ccattgtctc cctttaatct tctcttttgt atacatttgt    720
tacccatggt gttctttgtt ccttttcata agctaatacc actgtaggga ttttgttttg    780
aacgcatatt gacagcacgc tttacttagt agccggttcc catttgccat acaatgtagg    840
ttctgcttaa tgtaacttct tttttgctta agcatttgca tgactattag tgcttcaaag    900 tcaatttta aaaatgcaca agttataaat acagaagaaa gagcaaccca ccaaacctaa     960
caaggacccc cgaacacttt catactaaga ctgtaagtag atctcagttc tgcgtttatt   1020
gtaagttgat aaaacatct ggaagaaaat gactaaaact gtttgcatct ttgtatgtat    1080
ttattacttg atgtaataaa gcttatttc attaacaatt tgtattaaaa tgtgggttcc    1140
ttg                                                                 1143

<210> SEQ ID NO 7
<211> LENGTH: 871
<212> TYPE: DNA
<213> ORGANISM: Homo sapiens
<220> FEATURE:
<221> NAME/KEY: misc_feature
<222> LOCATION: (1)...(871)
<223> OTHER INFORMATION: n = A,T,C or G

<400> SEQUENCE: 7
acctgctggc ccctggacac ctctgtcacc atgtggttcc tggttctgtg cctcgccctg     60
tccctggggg ggactggtgc tgcgccccg attcagtccc ggattgtggg aggctgggag    120
tgtgagcagc attcccagcc ctggcaggcg cactggtca tggaaaacga attgttctgc     180
tcgggcgtcc tggtgcatcc gcagtgggtg ctgtcagccg cacactgttt ccagaactcc    240
tacaccatcg ggctgggcct gcacagtctt gaggccgacc aagagccagg agccagatg    300 gtggaggcca gcctctccgt acggcaccca gagtacaaca gacccttgct cgctaacgac    360
ctcatgntca tcaagttgga cgaatccgtg tccgagtctg acaacatccg gagnatcagc    420
attgnttcgc agtgccctac cgcggggaac ttttgcctcg tttctggctg gggtctgctg    480
gcgaacggca gaatgcctac cgtgctgcag tgcgtgaacg tgtcggtggt gtctgaggag    540
gtctgcagta agctctatga cccgctgtac cacccccagca tgttctgcgc cggcggaggg    600
caagaccaga aggactcctg caacggtgac tctgggggc ccctgatctg caacgggtac    660
ttgcagggcc ttgtgtcttt cggaaaagcc ccgtgtggcc aagttggcgt gccaggtgtc    720
tacaccaacc tctgcaaatt cactgagtgg ataagagaaaa ccgtccaggc cagttaactc    780
tggggactgg gaaccatga aattgacccc caaatacatc ctgcggaagg aattcaggaa    840
tatctgttcc cagcccctcc tccctcaggc c                                   871

<210> SEQ ID NO 8
<211> LENGTH: 1428
<212> TYPE: DNA
<213> ORGANISM: Homo sapiens

<400> SEQUENCE: 8
```

-continued

```
ggccggggttg ggggtgtgcg attgtgtggg acggtctggg gcagcccagc agcggctgac    60
cctctgcctg cggggaaggg agtcgccagg cggccgtcat ggcggtgtcg gagagccagc   120
tcaagaaaat ggtgtccaag tacaaataca gagacctaac tgtacgtgaa actgtcaatg   180
ttattactct atacaaagat ctcaaacctg ttttggattc atatgttttt aacgatggca   240
gttccaggga actaatgaac ctcactggaa caatccctgt gccttataga ggtaatacat   300
acaatattcc aatatgccta tggctactgg acacataccc atataatccc cctatctgtt   360
ttgttaagcc tactagttca atgactatta aaacaggaaa gcatgttgat gcaaatggga   420
agatatatct tccttatcta catgaatgga acacccaca gtcagacttg ttggggctta    480
ttcaggtcat gattgtggta tttggagatg aacctccagt cttctctcgt cctatttcgg   540
catcctatcc gccataccag gcaacgggc accaaatac ttcctacatg ccaggcatgc     600
caggtggaat ctctccatac ccatccggat accctcccaa tcccagtggt tacccaggct   660
gtccttaccc acctggtggt ccatatcctg ccacaacaag ttctcagtac ccttctcagc   720
ctcctgtgac cactgttggt cccagtaggg atggcacaat cagcgaggac accatccgag   780
cctctctcat ctctgcggtc agtgacaaac tgagatggcg gatgaaggag gaaatggatc   840
gtgcccaggc agagctcaat gccttgaaac aacagaaga agacctgaaa aagggtcacc   900
agaaactgga agagatggtt accgttttag atcaagaagt agccgaggtt gataaaaaca   960 tagaacttt gaaaagaag gatgaagaac tcagttctgc tctggaaaaa atggaaaatc     1020
agtctgaaaa caatgatatc gatgaagtta tcattcccac agctccctta tacaaacaga   1080
tcctgaatct gtatgcagaa gaaaacgcta ttgaagacac tatcttttac ttgggagaag   1140
ccttgagaag gggcgtgata gacctggatg tcttcctgaa gcatgtacgt cttctgtccc   1200
gtaaacagtt ccagctgagg gcactaatgc aaaaagcaag aaagactgcc ggtctcagtg   1260
acctctactg acttctctga taccagctgg aggttgagct cttcttaaag tattcttctc   1320
ttccttttat cagtaggtgc ccagaataag ttattgcagt ttatcattca mgtgtaaaat   1380
attttgaatc aataatatat tttctgtttt cttttggtaa agatggat                1428
```

<210> SEQ ID NO 9
<211> LENGTH: 667
<212> TYPE: DNA
<213> ORGANISM: Homo sapiens

<400> SEQUENCE: 9

```
ggctgagcgg ccccgcagcc aaccccgag gagcggccgg ctggcgtccg ccgcgcccag     60
gagttgggga tgtcctacaa acccatcgcc cctgctccca gcakcacccc tggctccagc   120 accctggc cgggcacccc ggtccctaca ggaagcgtcc cgtcgccgtc gggctcagtg     180
ccaggagccg cgctccttt cagaccgctg tttaacgact ttggaccgcc ttccatgggc    240
tacgtgcagg cgatgaagcc accggcgcc cagggctccc agagcaccta cacggacctg   300
ctgtcagtca tagaggagat gggcaaagag atccggccta cctatgctgg cagcaagagc   360
gccatggagc gcctgaagag aggtatcatc catgcccggg ccctagtcag agagtgcctg   420
gcagagacag agcggaacgc ccgcacgtaa caggaagcgc ctcggcctca gcgtctggac   480
ctatccggcc actgcagagc acccgcttct ccctggcctt catcccgagt tgcactaacc   540
atcctgggct tcctgtcctg tgtccctttgg tgggtcccct ccaggaacca aggagtggcc   600
ctccaggtgg cagcactaag gacacccccc cacaacaaga gttagcagcg aggtccccat   660
gagtccc                                                             667
```

```
<210> SEQ ID NO 10
<211> LENGTH: 397
<212> TYPE: DNA
<213> ORGANISM: Homo sapiens
<220> FEATURE:
<221> NAME/KEY: misc_feature
<222> LOCATION: (1)...(397)
<223> OTHER INFORMATION: n = A,T,C or G

<400> SEQUENCE: 10
ctgaactcta cctggtgacc agggaccagg acctttataa ggtggaaggc ttgatgtcct         60
ccccagactc agctcctggt gaagctccca gccatcagcc atgagggtct tgtatctcct        120
cttctcgttc ctcttcatat tcctgatgcc tcttccaggt gtttttggtg gtataggcga        180
tcccgttacc tgccttaaga gtggagccat atgtcatcca gtcttttgcc ctagaaggta        240
taaacnaatt ggcacctgtg gtctccctgg aacaaaatgc tgnaaaaagc catgaggagg        300
ccaagaagct gctgtggcng angcggattc agaaagggct ccctcatcag agangtgcga        360
catgtaaacc aaattaaact atggtgtcca angatan                                 397
```